United States Patent
Radominska-Pandya et al.

(10) Patent No.: US 9,399,055 B2
(45) Date of Patent: *Jul. 26, 2016

(54) ANTI-CANCER NANOPARTICLE COMPOSITIONS AND METHODS OF USE

(71) Applicant: Board of Trustees of the University of Arkansas, Little Rock, AR (US)

(72) Inventors: Anna Radominska-Pandya, Little Rock, AR (US); Alexandru S. Biris, Little Rock, AR (US)

(73) Assignee: Board of Trustees of the University of Arkansas, Little Rock, AR (US)

( * ) Notice: Subject to any disclaimer, the term of this patent is extended or adjusted under 35 U.S.C. 154(b) by 53 days.

This patent is subject to a terminal disclaimer.

(21) Appl. No.: 14/336,492

(22) Filed: Jul. 21, 2014

(65) Prior Publication Data

US 2014/0328927 A1    Nov. 6, 2014

Related U.S. Application Data

(62) Division of application No. 13/073,270, filed on Mar. 28, 2011, now Pat. No. 8,883,218.

(60) Provisional application No. 61/446,844, filed on Feb. 25, 2011, provisional application No. 61/317,854, filed on Mar. 26, 2010.

(51) Int. Cl.
```
C12N 5/00      (2006.01)
C12N 5/02      (2006.01)
A61K 48/00     (2006.01)
A61K 38/45     (2006.01)
A61K 31/711    (2006.01)
A61K 38/17     (2006.01)
A61K 47/48     (2006.01)
B82Y 5/00      (2011.01)
A61K 9/00      (2006.01)
```

(52) U.S. Cl.
CPC .............. *A61K 38/45* (2013.01); *A61K 9/0092* (2013.01); *A61K 31/711* (2013.01); *A61K 38/17* (2013.01); *A61K 47/48853* (2013.01); *A61K 47/48861* (2013.01); *A61K 47/48869* (2013.01); *A61K 47/48884* (2013.01); *B82Y 5/00* (2013.01); *A61K 9/0019* (2013.01)

(58) Field of Classification Search
None
See application file for complete search history.

(56) References Cited

U.S. PATENT DOCUMENTS

| | | | |
|---|---|---|---|
| 4,241,046 A | 12/1980 | Papahadjopoulos et al. | |
| 4,394,448 A | 7/1983 | Szoka, Jr. et al. | |
| 4,529,561 A | 7/1985 | Hunt et al. | |
| 4,755,388 A | 7/1988 | Heath et al. | |
| 4,828,837 A | 5/1989 | Uster et al. | |
| 4,925,661 A | 5/1990 | Huang | |
| 4,954,345 A | 9/1990 | Muller | |
| 4,957,735 A | 9/1990 | Huang | |
| 5,043,164 A | 8/1991 | Huang et al. | |
| 5,064,655 A | 11/1991 | Uster et al. | |
| 5,077,211 A | 12/1991 | Yarosh | |
| 5,264,618 A | 11/1993 | Felgner et al. | |
| 6,136,839 A | 10/2000 | Isakson et al. | |
| 6,448,450 B1 | 9/2002 | Nag et al. | |
| 6,552,085 B2 | 4/2003 | Inman et al. | |
| 6,710,037 B2 * | 3/2004 | Bond et al. .................. 514/44 R |
| 7,384,920 B2 | 6/2008 | Li et al. | |
| 8,410,064 B2 | 4/2013 | Radominska-Pandya et al. | |
| 8,883,218 B2 | 11/2014 | Radominska-Pandya et al. | |
| 2002/0198167 A1 | 12/2002 | Czernik et al. | |
| 2003/0215462 A1 | 11/2003 | Wacher et al. | |
| 2005/0074745 A1 | 4/2005 | Clayton et al. | |
| 2006/0153808 A1 | 7/2006 | Cristofanilli et al. | |
| 2006/0275371 A1 | 12/2006 | Dai et al. | |
| 2007/0259894 A1 | 11/2007 | Kassahun | |
| 2010/0226856 A1 | 9/2010 | Vitaliano et al. | |
| 2010/0273203 A1 | 10/2010 | Miller et al. | |
| 2011/0046081 A1 | 2/2011 | Radominska-Pandya et al. | |
| 2011/0236495 A1 | 9/2011 | Radominska-Pandya et al. | |
| 2012/0165280 A1 | 6/2012 | Mayeux et al. | |
| 2012/0165281 A1 | 6/2012 | Radominska-Pandya et al. | |
| 2012/0184536 A1 | 7/2012 | Radominska-Pandya | |

FOREIGN PATENT DOCUMENTS

| | | | |
|---|---|---|---|
| WO | 99/59561 A2 | 11/1999 | |
| WO | 2011/017456 A2 | 2/2011 | |
| WO | 2011/026112 A1 | 3/2011 | |

OTHER PUBLICATIONS

Prato et al. Acc. Chem. Res., 2008, 41 (1), pp. 60-68.*
Bianco et al., Current Opinion in Chemical Biology 2005, 9:674-679.*
Lacerda et al., NanoToday, vol. 2, Issue 6, Dec. 2007, pp. 38-43.*
Little et al., "Characterization of Human Liver Microsomal UDP-Glycosyltransferases using Photoaffinity Analogs", The Journal of Pharmacology and Experimental Therapeutics, 1995, pp. 1551-1559, vol. 273, No. 3.
Little et al., "Glucuronidation of oxidized fatty acids and prostaglandins B1 and E2 by human hepatic and recombinant UDP-glucuronosyltransferases", Journal of Lipid Research, 2004, pp. 1694-1703, vol. 45.
Liu et al., "Functional CB1 cannabinoid receptors in human vascular endothelial cells", Biochemical Journal, 2000, pp. 835-840, vol. 346.
Locatelli et al., "Determination of warfarin enantiomers and hydroxylated metabolites in human blood plasma by liquid chromatography with achiral and chiral separation", Journal of Chromatography B, 2005, pp. 191-198, vol. 818.

(Continued)

*Primary Examiner* — Doug Schultz

(57) ABSTRACT

The present invention encompasses a composition capable of delivering and expressing a nucleic acid encoding UDP-Glucuronosyltransferases, p53 or a combination thereof into a cell, and methods for treating tumors.

12 Claims, 10 Drawing Sheets

(8 of 10 Drawing Sheet(s) Filed in Color)

(56) References Cited

OTHER PUBLICATIONS

Lyle et al., "Synthesis and Characterization of Glucuronides of Cannabinol, Cannabidiol, Δ9-Tetrahydrocannabinol and Δ8-Tetrahydrocannabinol", Biomedical Mass Spectrometry, 1977, pp. 190-196, vol. 4, No. 3.

Matsuda et al., "Structure of a cannabinoid receptor and functional expression of the cloned cDNA", Nature, 1990, pp. 561-564, vol. 346.

Merck Manual, Sixteenth Edition, 1992, pp. 446-447; 522-523; and 1274.

Miley et al., "Crystal Structure of the Cofactor-Binding Domain of the Human Phase II Drug-Metabolism Enzyme UDP-Glucuronosyltransferase 2B7", J. Mol. Biol., 2007, pp. 498-511, vol. 369, No. 2.

Miller et al., "Identification of Hydroxywarfarin Binding Site in Human UDP Glucuronosyltransferase 1A10: Phenylalanine90 is Crucial for the Glucuronidation of 6- and 7-Hydroxywarfarin but Not 8-Hydroxywarfarin", Drug Metabolism and Disposition, 2008, pp. 2211-2218, vol. 36, No. 11.

Miller et al., "Assessing Cytochrome P450 and UDP-Glucuronosyltransferase Contributions to Warfarin Metabolism in Humans", Chem. Res. Toxicol., 2009, pp. 1239-1245, vol. 22, No. 7.

Moran et al., "LC-Ms/ms Characterization of Warfarin Metabolites Excreted in Human Urine", Oct. 2008, Abstracts, 64th Southwest Regional Meeting of the ACS, 1 pg.

Munro et al., "Molecular characterization of a peripheral receptor for cannabinoids", Nature, 1993, pp. 61-65, vol. 365, No. 6441.

Naef et al., "The analgesic effect of oral delta-9-tetrahydrocannabinol (THC), morphine, and a THC-morphine combination in healthy subjects under experimental pain conditions", Pain, 2003, pp. 79-88, vol. 105.

Newton et al., "Cytochrome P450 Inhibitors: Evaluation of Specificities in the In Vitro Metabolism of Therapeutic Agents by Human Liver Microsomes", Drug Metabolism and Disposition, 1995, pp. 154-158, vol. 23, No. 1.

Ngui et al., "In Vitro Stimulation of Warfarin Metabolism by Quinidine: Increases in the Formation of 4'- and 10-Hydroxywarfarin", Drug Metabolism and Disposition, 2001, pp. 877-886, vol. 29, No. 6.

Notice of Allowability from related U.S. Appl. No. 13/073,270, dated Oct. 10, 2014; 7 pgs.

Notice of Allowance from related U.S. Appl. No. 13/073,270, dated Apr. 21, 2014; 7 pgs.

Notice of Allowance from related U.S. Appl. No. 12/862,501, dated Dec. 3, 2012; 5 pgs.

Nyu Medical Center, Patient & Family Education, "Managing Your Warfarin (Coumadin®) Therapy, A Patient's Guide", Mar. 2002, 15 pgs.

Offen et al., "Structure of a flavonoid glucosyltransferase reveals the basis for plant natural product modification", The EMBO Journal, 2006, pp. 1396-1405, vol. 25, No. 6.

Office Action from related U.S. Appl. No. 13/073,270, dated Dec. 17, 2013; 11 pgs.

Office Action from related U.S. Appl. No. 13/073,270, dated May 30, 2013; 11 pgs.

Office Action from related U.S. Appl. No. 13/073,270, dated Nov. 20, 2012; 12 pgs.

Office Action from related U.S. Appl. No. 12/766,635, dated Oct. 28, 2013; 17 pgs.

Office Action from related U.S. Appl. No. 12/766,635, dated Apr. 17, 2013; 16 pgs.

Office Action from related U.S. Appl. No. 12/766,635, dated Aug. 1, 2012; 12 pgs.

Office Action from related U.S. Appl. No. 12/862,501, dated Jun. 21, 2012; 10 pgs.

Office Action from related U.S. Appl. No. 13/339,163, dated Dec. 24, 2014; 25 pgs.

Office Action from related U.S. Appl. No. 13/339,163, dated Aug. 6, 2014; 17 pgs.

Office Action from related U.S. Appl. No. 13/339,163, dated Jan. 29, 2014; 19 pgs.

Office Action from related U.S. Appl. No. 13/339,163, dated Jul. 12, 2013; 15 pgs.

Office Action from related U.S. Appl. No. 13/406,177, dated Nov. 21, 2013; 10 pgs.

Office Action from related U.S. Appl. No. 13/406,177, dated Mar. 13, 2013; 14 pgs.

Olas et al., "Comparative studies of the antioxidant effects of a naturally occurring resveratrol analogue—trans-3,3',5,5'-tetrahydroxy-4'-methoxystilbene and resveratrol—against oxidation and nitration of biomolecules in blood platelets", Cell Biol. Toxicol., 2008, pp. 331-340, vol. 24.

O'Reilly, "Interaction of the Anticoagulant Drug Warfarin and Its Metabolites with Human Plasma Albumin", The Journal of Clinical Investigation, 1969, pp. 193-202, vol. 48.

Panyam et al., "Biodegradable nanoparticles for drug and gene delivery to cells and tissue", Advanced Drug Delivery Reviews, 2003, pp. 329-347, vol. 55.

Paul et al., "Synthesis and Characterization of a New Class of Inhibitors of Membrane-associated UDP-Glycosyltransferases", The Journal of Biological Chemistry, 1993, pp. 12933-12938, vol. 268, No. 17.

Prato et al., "Functionalized Carbon Nanotubes in Drug Design and Discovery", Accounts of Chemical Research, 2008, pp. 60-68, vol. 41, No. 1.

Racz et al., "A Critical Role for the Cannabinoid CB1 Receptors in Alcohol Dependence and Stress-Stimulated Ethanol Drinking", The Journal of Neuroscience, 2003, pp. 2453-2458, vol. 23, No. 6.

Radominska et al., "Characterization of UDP-glucuronic acid transport in rat liver microsomal vesicles with photoaffinity analogs", Biochimica et Biophysica Acta, 1994, pp. 63-70, vol. 1195.

Radominska et al., "Photoaffinity labeling for evaluation of uridinyl analogs as specific inhibitors of rat liver microsomal UDP-glucuronosyltransferases", Biochimica et Biophysica Acta, 1994, pp. 336-345, vol. 1205.

Radominska-Pandya et al., "Structural and Functional Studies of UDP-Glucuronosyltransferases", Drug Metabolism Reviews, 1999, pp. 817-899, vol. 31, No. 4.

Radominska-Pyrek et al., "Glucuronidation of 6α-Hydroxy Bile Acids by Human Liver Microsomes", J. Clin. Invest., 1987, pp. 234-241, vol. 80.

Au et al., "Pharmacogenomics of 4-Hydroxycoumarin Anticoagulants", Drug Metabolism Reviews, 2008, pp. 355-375, vol. 40.

Ban Field et al., "Phenylbutazone-Warfarin Interaction in Man: Further Stereochemical and Metabolic Considerations", British Journal of Clinical Pharmacology, 1983, pp. 669-675, vol. 16.

Barbier et al., "3'-Azido-3'-Deoxythimidine (AZT) is Glucuronidated by Human UDP-Glucuronosyltransferase 2B7 (UGT2B7)", Drug Metabolism and Disposition, 2000, pp. 497-502, vol. 28, No. 5.

Barua et al., "Chemical synthesis and growth-promoting activity of all-trans-retinyl β-D-glucuronide", Biochemical Journal, 1987, pp. 231-234, vol. 244.

Battaglia et al., "Characterization of a new class of inhibitors of the recombinant human liver UDP-glucuronosyltransferase, UGT1*6", Biochimica et Biophysica Acta, 1995, pp. 9-14, vol. 1243.

Bianco et al., "Applications of carbon nanotubes in drug delivery", Current Opinion in Chemical Biology, 2005, pp. 674-679, vol. 9.

Bristol-Myers, "Medication Guide for Coumadin Tablets (Warfarin Sodium Tablets, USP) Crystalline", distributed by Bristol-Myers Squibb, Jan. 2009, 6 pgs.

Brotchie, "CB1 cannabinoid receptor signalling in Parkinson's disease", Current Opinion in Pharmacology, 2003, pp. 54-61, vol. 3, No. 1 (Abstract only).

Chan et al., "Disposition of warfarin enantiomers and metabolites in patients during multiple dosing with rac-warfarin", Br. J. Clin. Pharmac., 1994, pp. 563-569, vol. 37.

Cooper et al., "A genome-wide scan for common genetic variants with a large influence on warfarin maintenance dose", Blood, 2008, pp. 1022-1027, vol. 112, No. 4.

(56) References Cited

OTHER PUBLICATIONS

Court et al., "Evaluation of 3'-Azido-3'-Deoxythymidine, Morphine, and Codeine as Probe Substrates for UDP-Glucuronosyltransferase 2B7 (UGT2B7) in Human Liver Microsomes: Specificity and Influence of the UGT2B7*2 Polymorphism", Drug Metabolism and Disposition, 2003, pp. 1125-1133, vol. 31, No. 9.
Dettmer et al., "Mass Spectrometry-Based Metabolomics", Mass. Spectrom. Rev., 2007, pp. 51-78, vol. 26, No. 1.
Eble et al., "A comparison of the isomers of warfarin*", Biochemical Pharmacology, 1966, pp. 1003-1006, vol. 15.
Egan et al., "Rapid and sensitive determination of coumarin and 7-hydroxycoumarin and its glucuronide conjugate in urine and plasma by high-performance liquid chromatography", Journal of Chromatography, 1992, pp. 137-143, vol. 582.
Galiegue et al., "Expression of central and peripheral cannabinoid receptors in human immune tissues and leukocyte subpopulations", European Journal of Biochemistry, 1995, pp. 54-61, vol. 232.
Gall et al., "Differential glucuronidation of bile acids, androgens and estrogens by human UGT1A3 and 2B7", Journal of Steroid Biochemistry and Molecular Biology, 1999, pp. 101-108, vol. 70.
Gallup et al., "Effects of retinoid beta-glucuronides and N-retinoyl amines on the differentiation of HL-60 cells in vitro", Proc. Soc. Exp. Biol. Med., 1987, pp. 269-274, vol. 186, No. 3 (Abstract only).
Gebauer, "Synthesis and structure-activity relationships of novel warfarin derivatives", Bioorg. & Med. Chem., 2007, pp. 2414-2420, vol. 15.
Grancharov et al., "Natural and synthetic inhibitors of UDP-glucuronosyltransferase", Pharmacology & Therapeutics, 2001, pp. 171-186, vol. 89.
Gustafson et al., "Validated method for the simultaneous determination of Δ9-tetrahydrocannibol (THC), 11-hydroxy-THC and 11-nor-9-carboxy-THC in human plasma using solid phase extraction and gas chromatography—mass spectrometry with positive chemical ionization", Journal of Chromatography B, 2003, pp. 145-154, vol. 798.
Haining et al., "Allelic Variants of Human Cytochrome P450 2C9: Baculovirus-Mediated Expression, Purification, Structural Characterization, Substrate Stereoselectivity and Prochiral Selectivity of the Wild-Type and I359L Mutant Forms", Archives of Biochemistry and Biophysics, 1996, pp. 447-458, vol. 333, No. 2.
Hirsh et al., "Oral Anticoagulants: Mechanism of Action, Clinical Effectiveness, and Optimal Therapeutic Range", Chest, 2001, pp. 8S-21S, vol. 119.
Holbrook et al., "Systematic Overview of Warfarin and Its Drug and Food Interactions", Arch. Intern. Med., 2005, pp. 1095-1106, vol. 165.
Howlett, "Pharmacology of Cannabinoid Receptors", Annual Review of Pharmacology and Toxicology, 1995, pp. 607-634, vol. 35.
Hyland et al., "In vitro and in vivo glucuronidation of midazolam in humans", British Journal of Clinical Pharmacology, 2009, pp. 445-454, vol. 67, No. 4.
International Search Report and Written Opinion from related International Patent Application No. PCT/US2010/047340, mailed Oct. 26, 2010; 7 pgs.
International Search Report and Written Opinion from related International Patent Application No. PCT/US2012/026578, mailed Jun. 6, 2012; 10 pgs.
Iversen et al., "Cannabinoids: a real prospect for pain relief?", Current Opinion in Pharmacology, 2002, pp. 50-55, vol. 2.
Janick-Buckner et al., "Induction of HL-60 cell differentiation by water-soluble and nitrogen-containing conjugates of retinoic acid and retinol", The FASEB Journal, 1991, pp. 320-325, vol. 5.
Jansing et al., "Phase II Metabolism of Warfarin in Primary Culture of Adult Rat Hepatocytes", Mol. Pharmacol., 1991, pp. 209-215, vol. 41.
Jones et al., "Warfarin and UDP-glucuronosyltransferases: writing a new chapter of metabolism", Drug Metabolism Reviews, 2010, pp. 55-61, vol. 42, No. 1.
Kaminsky et al., "Correlation of Human Cytochrome P4502C Substrate Specificities with Primary Structure: Warfarin as a Probe", Molecular Pharmacology, 1992, pp. 234-239, vol. 43.
Kaminsky et al., "Human P450 Metabolism of Warfarin", Pharmacol. Ther., 1997, pp. 67-74, vol. 73, No. 1.
Klein et al., "The cannabinoid system and immune modulation", Journal of Leukocyte Biology, 2003, pp. 486-496, vol. 74.
Kurkela et al., "Expression and Characterization of Recombinant Human UDP-glucuronosyltransferases (UGTs)", The Journal of Biological Chemistry, 2003, pp. 3536-3544, vol. 278, No. 6.
Kuuranne et al., "Glucuronidation of Anabolic Androgenic Steroids by Recombinant Human UDP-Glucuronosyltransferases", Drug Metabolism and Disposition, 2003, pp. 1117-1124, vol. 31, No. 9.
Kuzmic, "Program DYNAFIT for the Analysis of Enzyme Kinetic Data: Application to HIV Proteinase", Analytical Biochemistry, 1996, pp. 260-273, vol. 237, Article No. 0238.
Lacerda et al., "Cell-penetrating CNTs for delivery of therapeutics", Nanotoday, 2007, pp. 38-43, vol. 2, No. 6.
Larkin et al., "Clustal W and Clustal X version 2.0", Bioinformatics, 2007, pp. 2947-2948, vol. 23, No. 21.
Lee et al., "Metabolism of Vitamin K and Vitamin K 2,3-Epoxide via Interaction with a Common Disulfide", Biochemistry, 1984, pp. 2246-2252, vol. 23, No. 10.
Lesko, "The Critical Path of Warfarin Dosing: Finding an Optimal Dosing Strategy Using Pharmacogenetics", Clinical Pharmacology & Therapeutics, 2008, pp. 301-303, vol. 84, No. 3.
Limdi et al., "Kidney Function Influences Warfarin Responsiveness and Hemorrhagic Complications", J. Am. Soc. Nephrol., 2009, pp. 912-921, vol. 20.
Ravinet Trillou et al., "Anti-obesity effect of SR141716, a CB1 receptor antagonist, in diet-induced obese mice", Am. J. Physiol. Regul. Integr. Comp. Physiol., 2003, pp. R345-R353, vol. 284.
Rettie et al., "Hydroxylation of Warfarin by Human cDNA-Expressed Cytochrome P-450: A Role for P-4502C9 in the Etiology of (S)-Warfarin-Drug Interactions", Chem. Res. Toxicol., 1992, pp. 54-59, vol. 5.
Reynolds et al., "Individualizing warfarin therapy", Personalized Medicine, 2007, pp. 11-31, vol. 4, No. 1.
Ritter, "Roles of glucuronidation and UDP-glucuronosyltransferases in xenobiotic bioactivation reactions", Chemico-Biological Interactions, 2000, pp. 171-193, vol. 129.
Šali et al., "Comparative Protein Modelling by Satisfaction of Spatial Restraints", J. Mol. Biol., 1993, pp. 779-815, vol. 234, No. 3.
Smith et al., "Plasma pharmacokinetics of warfarin enantiomers in cats", Journal of Veterinary Pharmacology and Therapeutics, 2000, pp. 329-337, vol. 23, No. 6 (Abstract only), 1 pg.
Steward et al., "Genetic association between sensitivity to warfarin and expression of CYP2C9*3", Pharmacogenetics, 1997, pp. 361-367, vol. 7, No. 5 (Abstract only), 1 pg.
Takahashi et al., "Comparisons between in-vitro and in-vivo metabolism of (S)-warfarin: catalytic activities of cDNA-expressed CYP2C9, its Leu359 variant and their mixture versus unbound clearance in patients with the corresponding CYP2C9 genotypes", Pharmacogenetics, 1998, pp. 365-373, vol. 8, No. 5 (Abstract only), 2 pgs.
Wadelius et al., "Association of warfarin dose with genes involved in its action and metabolism", Hum. Genet., 2007, pp. 23-34, vol. 121.
Wang et al., "Identification of the Human Enzymes Involved in the Oxidative Metabolism of Dasatinib: An Effective Approach for Determining Metabolite Formation Kinetics", Drug Metabolism and Disposition, 2008, pp. 1828-1839, vol. 36, No. 9.
Weinmann et al., "Simultaneous determination of THC-COOH and THC-COOH-glucuronide in urine samples by LC / MS / MS", Forensic Science International, 2000, pp. 381-387, vol. 113.
Wen et al., "UDP-Glucuronosyltransferase 1A1 is the Principal Enzyme Responsible for Etoposide Glucuronidation in Human Liver and Intestinal Microsomes: Structural Characterization of Phenolic and Alcoholic Glucuronides of Etoposide and Estimation of Enzyme Kinetics", Drug Metabolism and Disposition, 2007, pp. 371-380, Vo. 35, No. 3.
Wienkers et al., "Formation of (R)-8-Hydroxywarfarin in Human Liver Microsomes: A New Metabolic Marker for the (S)-

(56) References Cited

OTHER PUBLICATIONS

Mephenytoin Hydroxylase, P4502C19", Drug Metabolism and Disposition, 1996, pp. 610-614, vol. 24, No. 5.

Wittwer et al., "Role of Morphine's Metabolites in Analgesia: Concepts and Controversies", The AAPS Journal, 2006, pp. E348-E352, vol. 8, No. 2, Article 39.

Wu et al., "Evidence for the Role of Reactive Nitrogen Species in Polymicrobial Sepsis-Induced Renal Peritubular Capillary Dysfunction and Tubular Injury", Journal of the American Society of Nephrology, 2007, pp. 1807-1815, vol. 18.

Xiong et al., "Phenylalanine 90 and 93 Are Localized within the Phenol Binding Site of Human UDP-Glucuronosyltransferase 1A10 as Determined by Photoaffinity Labeling, Mass Spectrometry, and Site-Directed Mutagenesis", Biochemistry, 2006, pp. 2322-2332, vol. 45, No. 7.

Yamamoto et al., "The Pharmacological Activity of Cannabinol and Its Major Metabolite, 11-Hydroxycannabinol", Chem. Pharm. Bull., 1987, pp. 2144-2147, vol. 35, No. 5.

Zhang et al., "Human Cytochromes P4501A1 and P4501A2: R-Warfarin Metabolism as a Probe", Drug Metabolism and Disposition, 1995, pp. 1339-1345, vol. 23, No. 12.

Zielinska et al., "Glucuronidation of Monohydroxylated Warfarin Metabolites by Human Liver Microsomes and Human Recombinant UDP-Glucuronosyltransferases", The Journal of Pharmacology and Experimental Therapeutics, 2008, pp. 139-148, vol. 324, No. 1.

\* cited by examiner

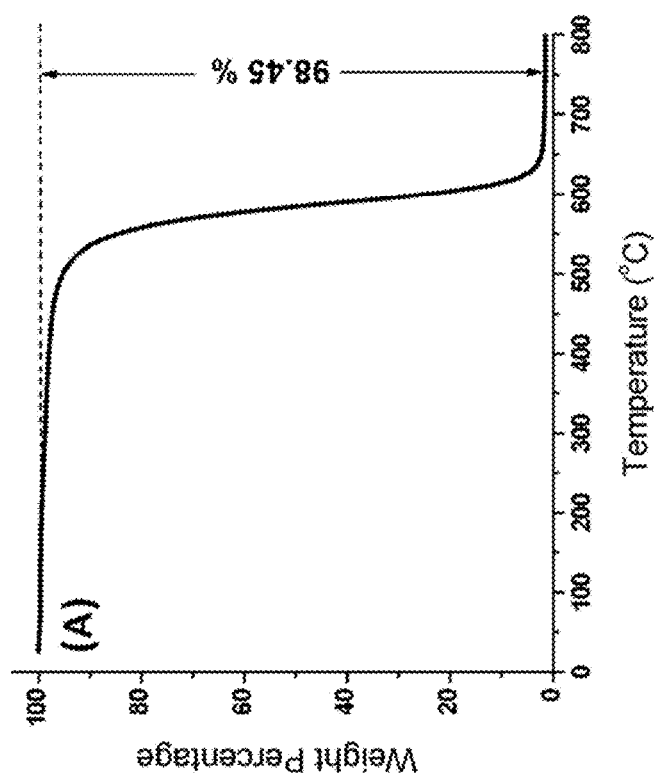
Fig. 3A
Fig. 3B

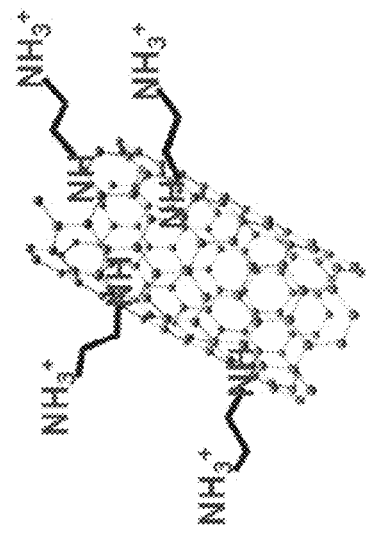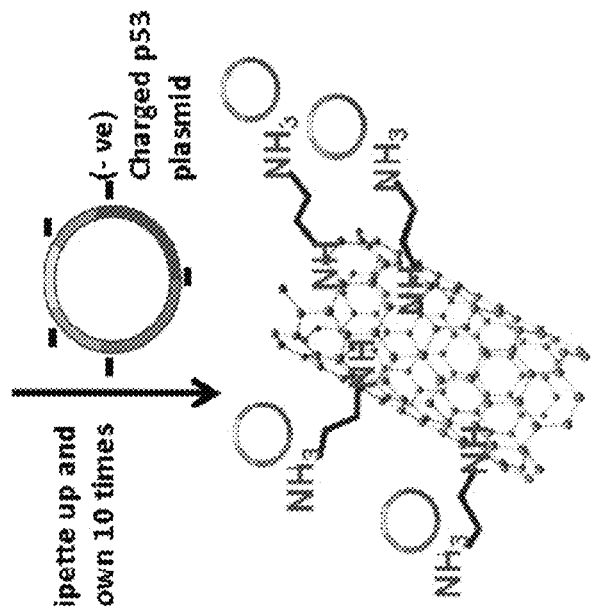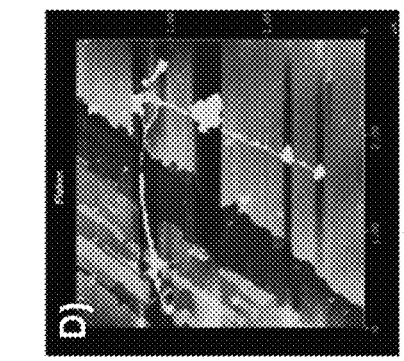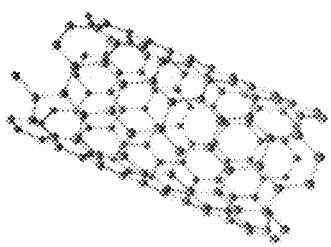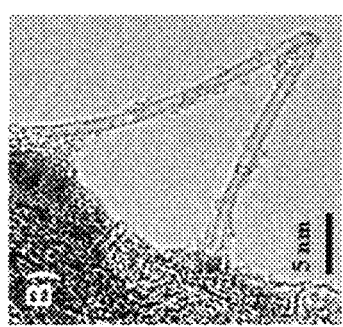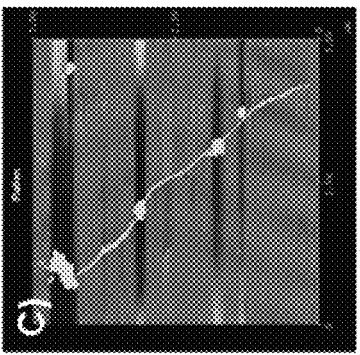
Fig. 4A
Fig. 4B
Fig. 4C
Fig. 4D

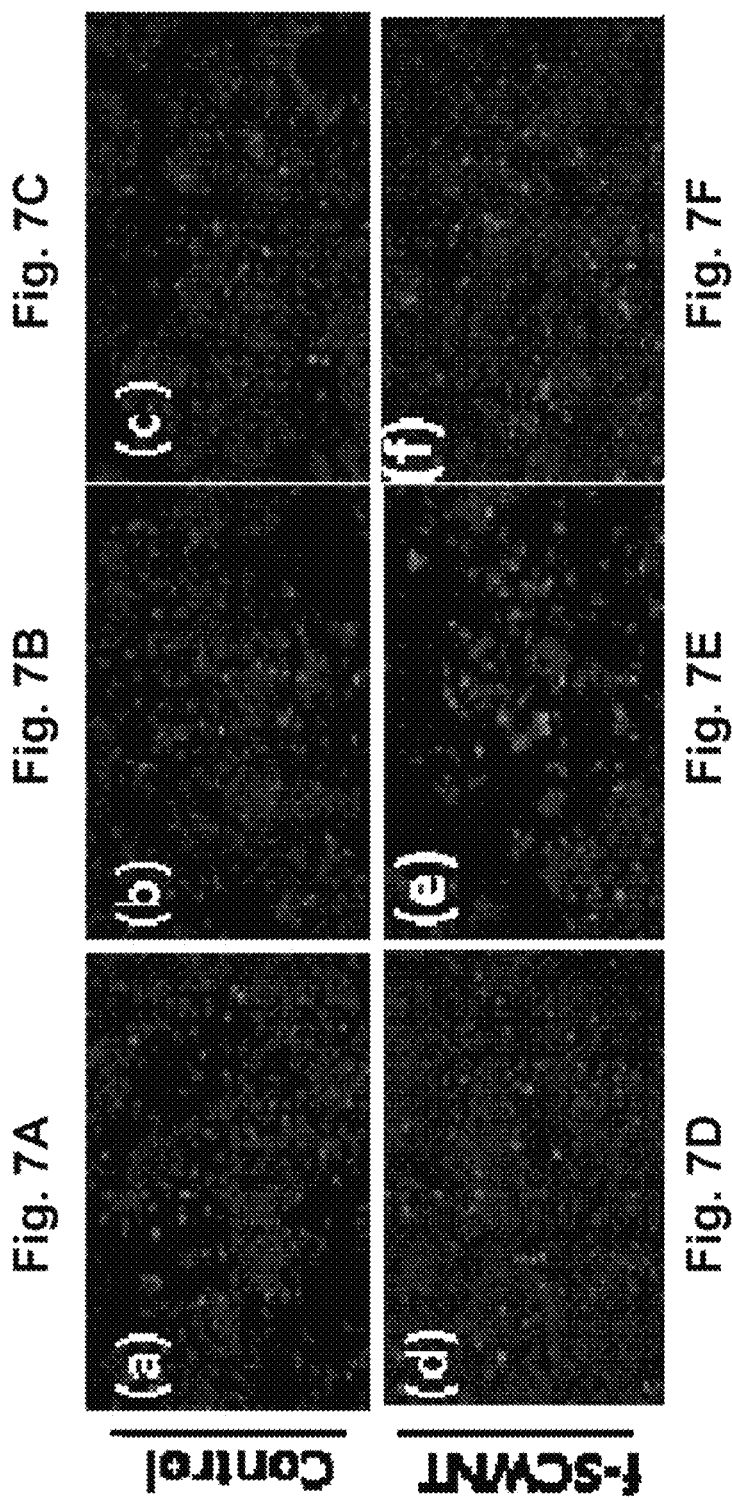

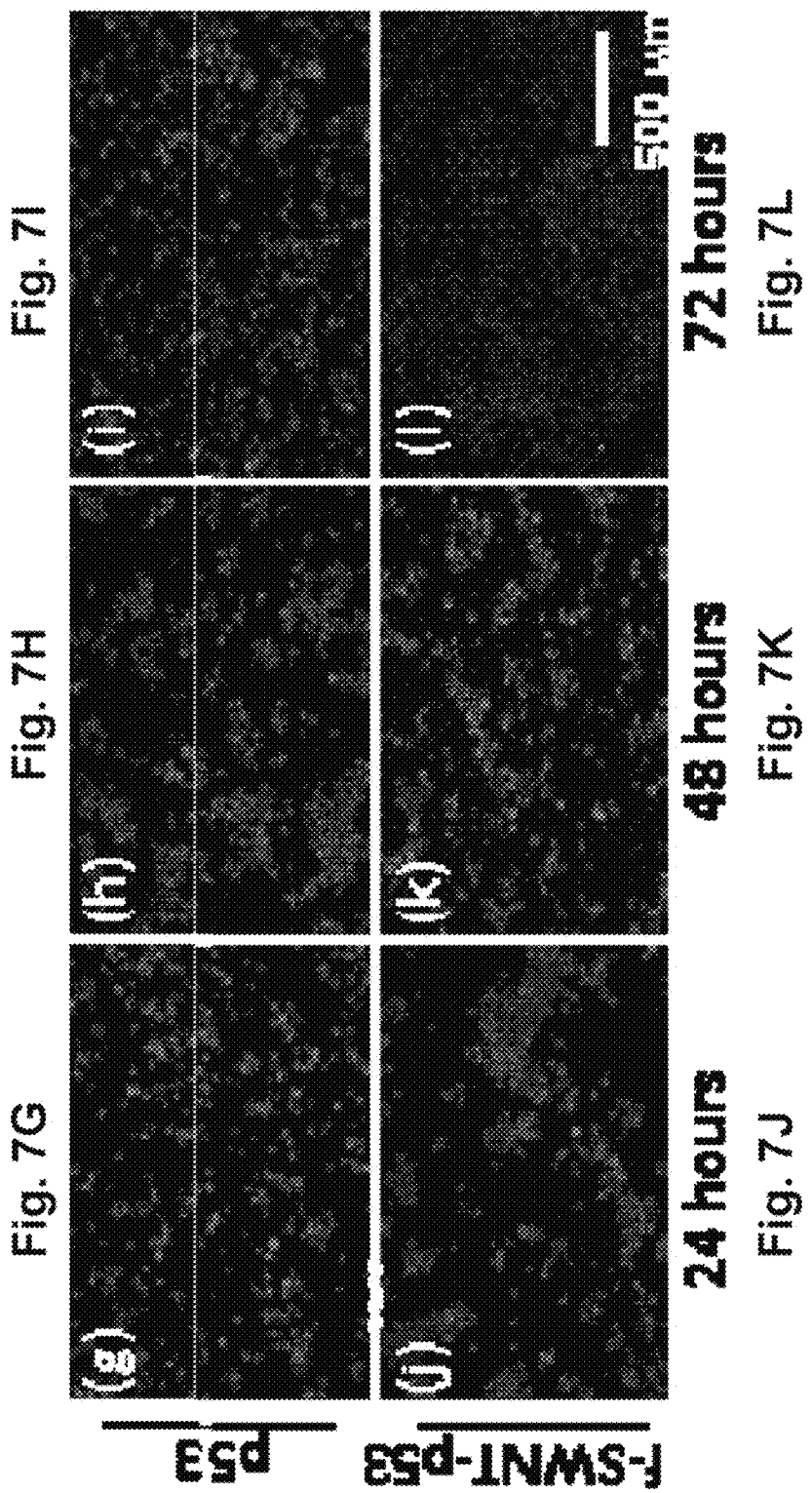

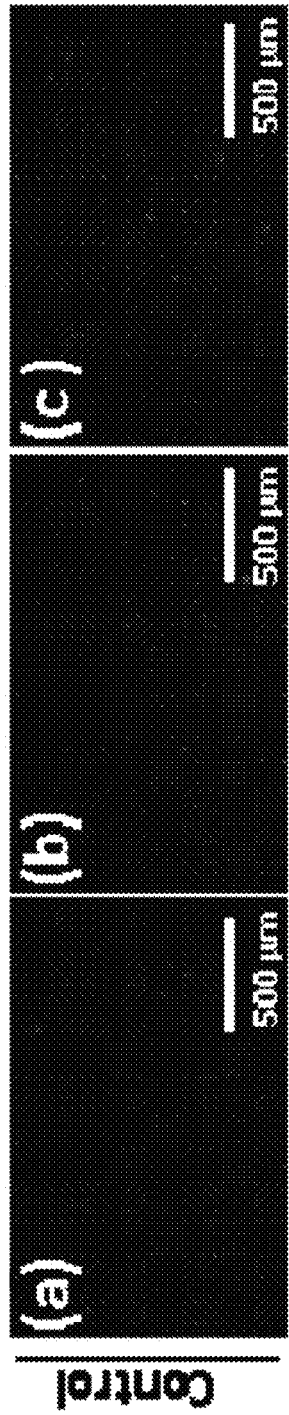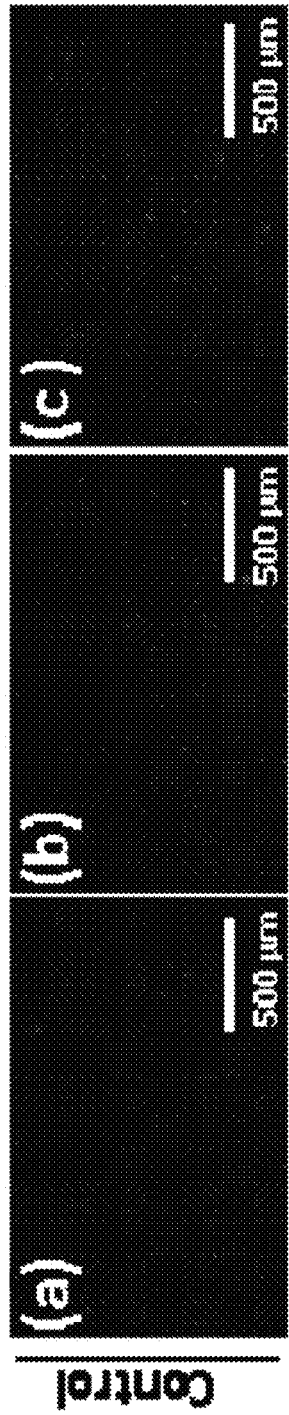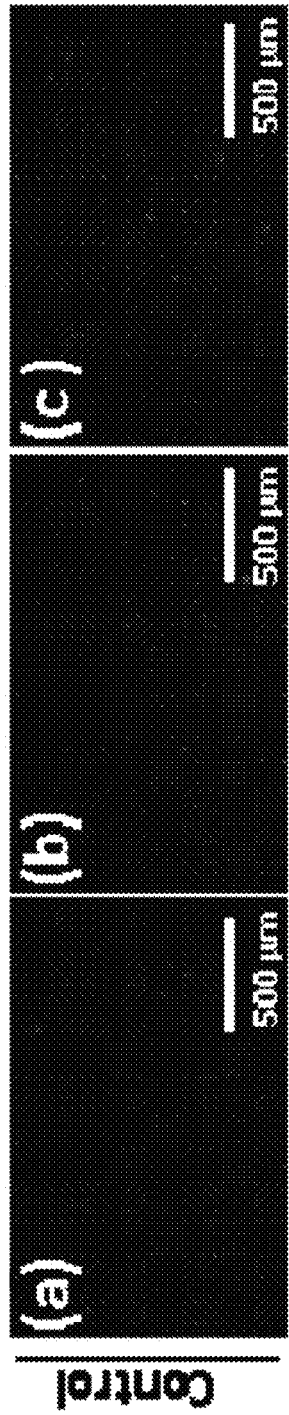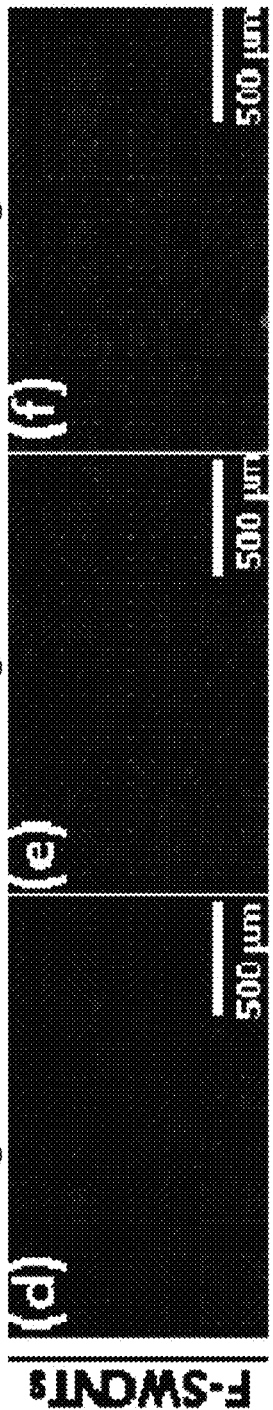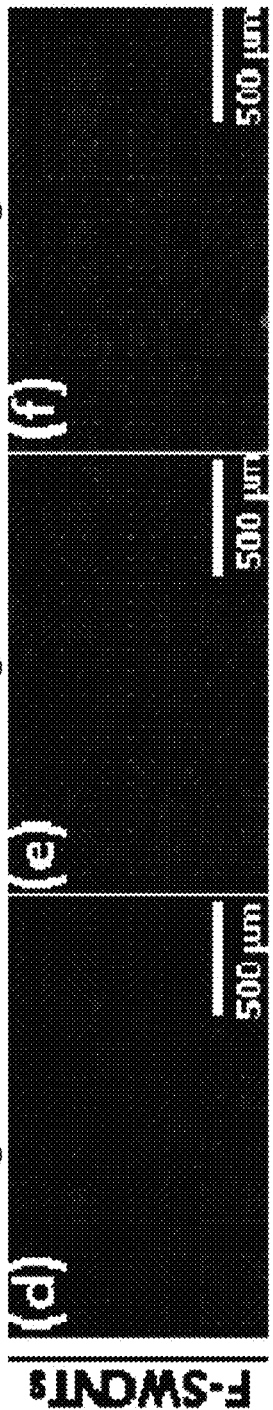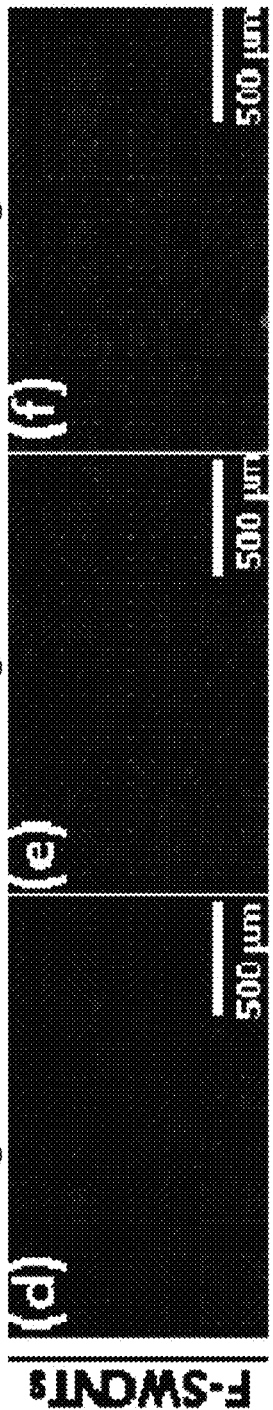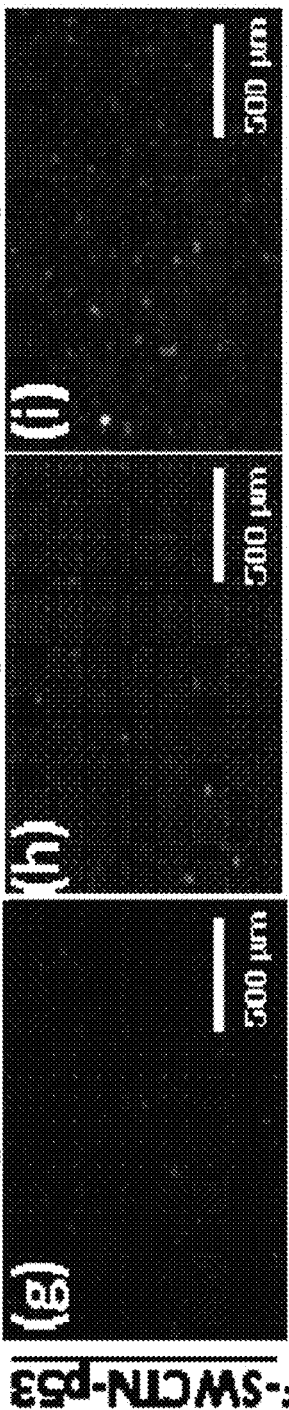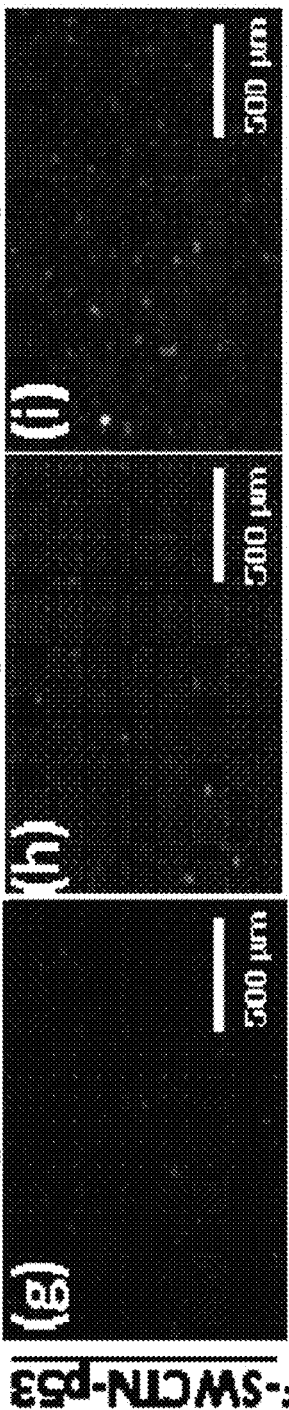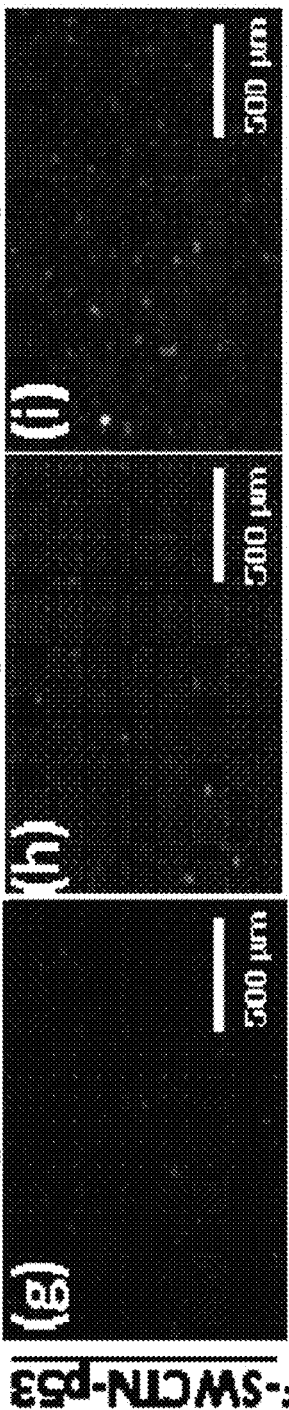

ANTI-CANCER NANOPARTICLE COMPOSITIONS AND METHODS OF USE

CROSS REFERENCE TO RELATED APPLICATIONS

This application is a divisional of US non-provisional application Ser. No. 13/073,270 filed Mar. 28, 2011 which claims the priority of U.S. provisional application 61/317,851, filed Mar. 26, 2010, and U.S. provisional application 61/446,844, filed Feb. 25, 2011, all of which are hereby incorporated by reference in its entirety.

GOVERNMENTAL RIGHTS

This invention was made with governmental support under GM075893 awarded by the National Institutes of Health. The government has certain rights in the invention.

FIELD OF THE INVENTION

The invention encompasses compositions and methods for delivering an anti-cancer nucleic acid to a cell.

BACKGROUND OF THE INVENTION

The majority of the current cancer treatment methods result in severe general toxicity to the human body. Both radiation and chemotherapy have deleterious effects to the host, causing significant morbidity and mortality. Hence, there is a need in the art for non-invasive and non-toxic methods of treating cancer and preventing tumor growth.

For instance, there is a need for compositions and methods that would introduce nucleic acids into a cell to restore pre-cancerous cell growth and metabolism. In particular, there is a need for compositions and methods that would allow the targeting of these anti-cancer nucleic acids to pre-cancerous or cancerous cells.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 3A shows a TGA analysis of the SWCNTs after purification and removal of amorphous carbon. FIG. 3B and the inset shows SEM images of the SWCNT bundles synthesized on the bimetallic catalyst system.

FIG. 4A shows a schematic representation of ethylenediamine functionalization of SWCNTs (f-SWCNTs) and formation of f-SWCNTs-p53 complex. FIG. 4B shows a TEM image of the SWCNTs. FIGS. 4C,D shows AFM images of f-SWCNTs-p53 complex formation.

FIG. 7 shows the effect of f-SWCNTs-delivered p53 on the induction of apoptosis via an ethidium bromide/acridine orange assay, where live cells are green and dead cells appear red when exposed to UV light. FIG. 7A-C show the control MCF-7 cells (without any treatment), FIG. 7D-F show the incubation of MCF-7 cells with f-SWCNTs, FIG. 7G-I show MCF-7 cells incubated with p53 plasmid, and FIG. 7J-L show the incubation of MCF-7 cells with f-SWCNTs and GFP tagged p53 plasmid complex.

FIG. 8 shows caspase-3 activity in MCF-7 cells. Specifically, FIG. 8A-C show the caspase activity in control cells (without any treatment), FIG. 8D-F show caspase activity in MCF-7 cells incubated with f-SWCNTs, FIG. 8G-I show caspase activity in MCF-7 cells incubated with f-SWCNTs and p53 plasmid complex for 24, 48, and 72 hours, respectively.

DETAILED DESCRIPTION OF THE INVENTION

Figure 1A:
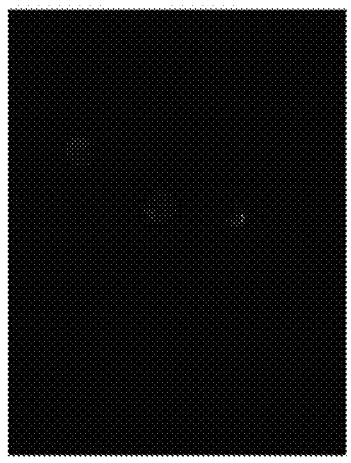
FIG. 1 depicts caspase 3 activity in pancreatic cancer cells (panc1 cells) incubated with the UGT plasmid attached to the single wall carbon nanotubes. (A) Control untreated Panc1 cells, (B) Panc1 cells incubated with Plasmid-nanotube composition, and (C) Panc1 cells incubated with nanotubes alone.

A composition capable of delivering an anti-cancer nucleic acid has been discovered. As used herein, "anti-cancer" refers to a nucleic acid whose expression may reduce cancer symptoms, prevent cancer symptoms, reduce tumor size or reduce metastasis. In some embodiments, an anti-cancer nucleic acid may encode a tumor suppressor protein. In certain embodiments, a composition is targeted to a tumor cell. In other embodiments, a composition is further incorporated into a vehicle for delivery to a cell. Each of these embodiments, as well as methods of using a composition of the invention, are discussed in more detail below.

I. Composition

One aspect of the invention encompasses a composition comprising at least one nucleic acid attached to a nanoparticle. In one embodiment, the invention encompasses a composition comprising at least one nucleic acid encoding a UDP-glucuronosyltransferase (UGT). In another embodiment, the invention encompasses a composition comprising at least one nucleic acid encoding p53. Other suitable nucleic acids and nanoparticles are discussed in further detail below.

(a) Nucleic Acid

Generally speaking, a nucleic acid of the invention comprises at least one anti-cancer nucleic acid. In some embodiments, a nucleic acid of the invention comprises more than one anti-cancer nucleic acid. For instance, a nucleic acid of the invention may comprise at least one, two, three, four, five, six, seven, eight, or nine anti-cancer nucleic acids. For example, in one embodiment, more than one anti-cancer nucleic acid may be expressed as a single fusion polypeptide. In another embodiment, more than one anti-cancer nucleic acid may be expressed as a single fusion polypeptide which is cleaved into the individual UGT polypeptides after translation. By way of non-limiting example, 2A peptides of picornaviruses inserted between anti-cancer nucleic acid polypeptides comprising a fusion protein may result in the co-translational 'cleavage' of the proteins and lead to expression of multiple proteins at equimolar levels. In another alternative, a nucleic acid may express a polycystronic transcript that is translated into separate anti-cancer nucleic acid proteins. As would be recognized in the art, such polycystronic expression in eukryotic cells may be achieved through internal ribosomal entry sites (IRES) for translation of an internal open reading frame. IRES elements allow a cap-independent translation mechanism in which an IRES element positioned 3' downstream of the open reading frame translated from the cap region of the mRNA is recognized by the ribosome, allowing translation of a second coding region from the transcript. IRES elements from virus and mammalian messages have been described. Non-limiting examples of IRES elements that may be used in the invention include IRES elements from poliovirus Type I, the 5'UTR of encephalomyocarditis virus (EMV), of Thelier's murine encephalomyelitis virus (TMEV), of foot and mouth disease virus (FMDV), of bovine enterovirus (BEV), of coxsackie B virus (CBV), of human rhinovirus (HRV), the human immunoglobulin heavy chain binding protein (BIP) 5'UTR, the *Drosophila* antennapediae 5'UTR, the *Drosophila* ultrabithorax 5'UTR, or genetic hybrids or fragments from the above. In preferred embodiments, the heterologous nucleic acid expresses a monocystronic transcript. In certain embodiments, a nucleic acid of the invention comprises one anti-cancer nucleic acid. Suitable anti-cancer nucleic acids include without limitation UGTs, p53, nucleic acids encoding tumor suppressor proteins, and anti-cancer nucleic acids known in the art.

Suitable anti-cancer nucleic acids of the invention may be derived from any organism comprising an anti-cancer nucleic acid, such as animals, plants and bacteria. In exemplary embodiments, a nucleic acid of the invention is derived from a human sequence. In certain embodiments, a nucleic acid of the invention comprises a tumor suppressor protein. Non-limiting examples of tumor suppressor proteins may include PTEN, APC, CD95, ST5, ST7, and ST14. In one embodiment, a nucleic acid may be a UGT isozyme. In another embodiment, a nucleic acid may be p53. Non-limiting examples of human UGT isozymes may include isozymes encoded by the following alleles: UGT1A1, UGT1A3, UGT1A4, UGT1A5, UGT1A6, UGT1A7, UGT1A8, UGT1A9, UGT1A10, UGT2A1, UGT2A2, UGT2A3, UGT2B4, UGT2B7, UGT2B10, UGT2B11, UGT2B15, UGT2B17, and UGT2B28. In one embodiment, a nucleic acid of the invention comprises a UGT1A3 isozyme. In another embodiment, a nucleic acid of the invention comprises a UGT1A4 isozyme. In yet another embodiment, a nucleic acid of the invention comprises a UGT1A5 isozyme. In another embodiment, a nucleic acid of the invention comprises a UGT1A6 isozyme. In a further embodiment, a nucleic acid of the invention comprises a UGT1A7 isozyme. In yet a further embodiment, a nucleic acid of the invention comprises a UGT1A8 isozyme. In still a further embodiment, a nucleic acid of the invention comprises a UGT1A9 isozyme. In an alternative embodiment, a nucleic acid of the invention comprises a UGT2A1 isozyme. In another alternative embodiment, a nucleic acid of the invention comprises a UGT2A2 isozyme. In yet another alternative embodiment, a nucleic acid of the invention comprises a UGT2A3 isozyme. In still another alternative embodiment, a nucleic acid of the invention comprises a UGT2B4 isozyme. In an additional embodiment, a nucleic acid of the invention comprises a UGT2B10 isozyme. In another additional embodiment, a nucleic acid of the invention comprises a UGT2B11 isozyme. In yet another additional embodiment, a nucleic acid of the invention comprises a UGT2B17 isozyme. In still another additional embodiment, a nucleic acid of the invention comprises a UGT2B28 isozyme. In an exemplary embodiment, a nucleic acid of the invention comprises a UGT1A1 isozyme. In another exemplary embodiment, a nucleic acid of the invention comprises a UGT2B7 isozyme. In yet another exemplary embodiment, a nucleic acid of the invention comprises a UGT1A10 isozyme. In still another exemplary embodiment, a nucleic acid of the invention comprises a UGT2B15 isozyme.

A nucleic acid comprising an anti-cancer nucleic acid may comprise DNA, RNA or a modified nucleic acid base. In some embodiments, a nucleic acid comprising an anti-cancer nucleic acid comprises RNA. For instance, a nucleic acid may comprise mRNA. When a nucleic acid comprises mRNA, the mRNA molecule may be 5' capped. Similarly, in some embodiments when a nucleic acid comprises mRNA, the mRNA molecule may be polyadenylated. In an exemplary embodiment, an mRNA molecule comprising an anti-cancer nucleic acid may be capped and polyadenylated. Methods of capping and polyadenylating mRNA are known in the art.

In preferred embodiments, a nucleic acid comprising an anti-cancer nucleic acid comprises DNA. When a nucleic acid encoding an anti-cancer nucleic acid is DNA, the nucleic acid typically comprises an expression cassette. As used herein, an "expression cassette" is a nucleic acid construct comprising a nucleic acid comprising an anti-cancer nucleic acid operably linked to a promoter (and perhaps other regulatory sequences) capable of expressing an anti-cancer nucleic acid in a target cell. As used herein, the term promoter may mean a synthetic or naturally-derived molecule capable of conferring or activating expression of a target nucleic acid sequence in a cell. The promoter and target sequence may be the promoter normally associated with a nucleic acid encoding an anti-cancer nucleic acid, or may be a heterologous promoter. A heterologous promoter may be derived from such sources as viruses, bacteria, fungi, plants, insects, and animals. A promoter may regulate the expression of a nucleic acid sequence constitutively or differentially with respect to the cell, the tissue or organ in which expression occurs. Or, a promoter may regulate expression with respect to developmental stage, or in response to external stimuli such as physiological stresses, pathogens, metal ions, or inducing agents or activators (i.e. an inducible promoter). Non-limiting representative examples of promoters may include the bacteriophage T7 promoter, bacteriophage T3 promoter, SP6 promoter, HSP70 basal promoter, lac operator-promoter, tac promoter, SV40 late promoter, SV40 early promoter, RSV-LTR promoter, CMV IE promoter, a promoter comprising the tetracycline response element (TRE) nucleic acid sequence, and the CMV IE promoter. In some embodiments, the promoter is the promoter normally associated with a nucleic acid encoding an anti-cancer nucleic acid of the invention. In other embodiments, the promoter is the SV40 promoter.

In some alternative embodiments, a nucleic acid comprising an anti-cancer nucleic acid is operably linked to a transcription termination sequence. A transcription termination sequence may be included to prevent inappropriate expression of nucleic acid sequences adjacent to the heterologous nucleic acid sequence.

In other embodiments, a nucleic acid comprising an anti-cancer nucleic acid of the invention is incorporated into a vector. One of skill in the art would be able to construct a vector through standard recombinant techniques (see, for example, Sambrook et al., 2001 and Ausubel et al., 1996, both incorporated herein by reference). Vectors include but are not limited to plasmids, cosmids, transposable elements, viruses (bacteriophage, animal viruses, and plant viruses), and artificial chromosomes (e.g., YACs), such as retroviral vectors (e.g. derived from Moloney murine leukemia virus vectors (MoMLV), MSCV, SFFV, MPSV, SNV etc), lentiviral vectors (e.g. derived from HIV-1, HIV-2, SIV, BIV, FIV etc.), adenoviral (Ad) vectors including replication competent, replication deficient and gutless forms thereof, adeno-associated viral (AAV) vectors, simian virus 40 (SV-40) vectors, bovine papilloma virus vectors, Epstein-Barr virus, herpes virus vectors, vaccinia virus vectors, Harvey murine sarcoma virus vectors, murine mammary tumor virus vectors, and Rous sarcoma virus vectors. In preferred embodiments, the vector is a plasmid. In an exemplary embodiment, the vector is the pSVL plasmid.

Nucleic acid sequences of the invention may be obtained using a variety of different techniques known in the art. The nucleotide sequences, as well as homologous sequences, may be isolated using standard techniques, purchased or obtained from a depository. Once the nucleotide sequence is obtained, it may be amplified for use in a variety of applications, using methods known in the art.

(b) Nanoparticle

A nucleic acid of the invention is attached to a nanoparticle. As used herein, "nanoparticle" is used to refer to a nanostructure that is typically between about 5 nM and 400 nM across the largest dimension of the structure. A nanoparticle of the invention may be spherical, tubular, cylindrical, cubic, hexagonal, dumbbell or any other shape that may be envisaged or built in a laboratory setting. A nanoparticle of the invention may typically be between about 5 nm and 400 nm across the largest dimension, but in some instances, may be bigger or smaller. In another embodiment, the average size of a plurality of nanoparticles in a composition may typically be between about 5 nm and 400 nm across the largest dimension. In one embodiment, the largest dimension of a nanoparticle of the invention may be between about 100 nm and about 300 nm. In another embodiment, the largest dimension of a nanoparticle may be between about 5, 10, 20, 30, 40, 50, 60, 70, 80, 90, 100, 110, 120, 130, 140, 150, 160, 170, 180, 190, 200, 210, 220, 230, 240, 250, 260, 270, 280, 290, or 300 nm. In some embodiments, the largest dimension may be greater than 400 nm, for instance, 500, 600, 700, 800, 900, 1000, 2000, 3000, 4000, 5000, 6000, 7000, 8000, 9000, 10,000, or greater than 10,000 nm. In certain embodiments where the nanoparticle is a nanotube or a nanorod, the diameter of the nanoparticle may be from about 0.5 nm to about 4 nm. In a particular embodiment where the nanoparticle is a nanotube or nanorod, the diameter of the nanoparticle may be from about 0.7 nm to about 3 nm.

In some embodiments, the nanoparticle is a carbon nanostructure. Non-limiting examples of carbon nanostructures may include, single, double and multiwall carbon nanotubes, fullerenes, graphenes, carbon nanorods, or carbon nanospheres. In other embodiments, the nanoparticle is a metal nanoparticle. Non-limiting examples of metal nanoparticles include gold, silver, palladium or titanium nanoparticles or combinations thereof. In yet other embodiments, the nanoparticle is a metal oxide nanoparticle. Non-limiting examples of metal oxide nanoparticles are MgO, $SiO_2$, $As_2O_3/Fe_3O$, $Fe_3O_4$, and titanium dioxide.

In other embodiments, the nanoparticle is a natural or artificial polymer. Polymer nanoparticles may be biodegradable, bioresorbable, or bioerodable polymers. Preferably, the nanoparticle is bio-compatible. Non-limiting examples of polymers that are considered to be biodegradable, bioresorbable, or bioerodable include, but are not limited to, albumin, collagen, gelatin and prolamines such as zein, polysaccharides such as alginate, cellulose derivatives and polyhydroxyalkanoates such as polyhydroxybutyrate aliphatic polyesters; poly(glycolic acid) and/or copolymers thereof (e.g., poly(glycolide trimethylene carbonate); poly(caprolactone glycolide); poly(lactic acid) and/or isomers thereof (e.g., poly-L(lactic acid) and/or poly-D (lactic acid) and/or copolymers thereof (e.g. DL-PLA), with and without additives (e.g. calcium phosphate glass), and/or other copolymers (e.g. poly (caprolactone lactide), poly(lactide glycolide), poly(lactic acid ethylene glycol); poly(ethylene glycol) (in its various weights, i.e. 2000 D, 4000 D, 6000 D, 8000 D, etc.); poly (ethylene glycol)diacrylate; poly(lactide); polyalkylene succinate; polybutylene diglycolate; polyhydroxybutyrate (PHB); polyhydroxyvalerate (PHV); polyhydroxybutyrate/polyhydroxyvalerate copolymer (PHB/PHV); poly(hydroxybutyrate-co-valerate); polyhydroxyalkaoates (PHA); polycaprolactone; poly(caprolactone-polyethylene glycol) copolymer; poly(valerolactone); polyanhydrides; poly (orthoesters) and/or blends with polyanhydrides; poly(anhydride-co-imide); polycarbonates (aliphatic); poly(hydroxylesters); polydioxanone; polyanhydrides; polyanhydride esters; polycyanoacrylates; poly(alkyl 2-cyanoacrylates); poly(amino acids); poly(phosphazenes); poly(propylene fumarate); poly(propylene fumarate-co-ethylene glycol); poly(fumarate anhydrides); fibrinogen; fibrin; gelatin; cellulose and/or cellulose derivatives and/or cellulosic polymers (e.g., cellulose acetate, cellulose acetate butyrate, cellulose butyrate, cellulose ethers, cellulose nitrate, cellulose propionate, cellophane); chitosan and/or chitosan derivatives (e.g., chitosan NOCC, chitosan NOOC-G); alginate; polysaccharides; starch; amylase; collagen; polycarboxylic acids; poly (ethyl ester-co-carboxylate carbonate) (and/or other tyrosine derived polycarbonates); poly(iminocarbonate); poly(BPA-iminocarbonate); poly(trimethylene carbonate); poly(iminocarbonate-amide) copolymers and/or other pseudo-poly (amino acids); poly(ethylene glycol); poly(ethylene oxide); poly(ethylene oxide)/poly(butylene terephthalate) copolymer; poly(epsilon-caprolactone-dimethyltrimethylene carbonate); poly(ester amide); poly(amino acids) and conventional synthetic polymers thereof; poly(alkylene oxalates); poly(alkylcarbonate); poly(adipic anhydride); nylon copolyamides; NO-carboxymethyl chitosan NOCC); carboxymethyl cellulose; copoly(ether-esters) (e.g., PEO/PLA dextrans); polyketals; biodegradable polyethers; biodegradable polyesters; polydihydropyrans; polydepsipeptides; polyarylates (L-tyrosine-derived) and/or free acid polyarylates; polyamides (e.g., Nylon 66, polycaprolactam); poly(propylene fumarate-co-ethylene glycol) (e.g., fumarate anhydrides); hyaluronates; poly-p-dioxanone; polypeptides and proteins; polyphosphoester; polyphosphoester urethane; polysaccharides; pseudo-poly(amino acids); starch; terpolymer; (copolymers of glycolide, lactide, or dimethyltrimethylene carbonate); rayon; rayon triacetate; latex; and/pr copolymers, blends, and/or composites of above.

Non-limiting examples of polymers that are considered to be biostable include, but are not limited to, parylene; parylene c; parylene f; parylene n; parylene derivatives; maleic anyhydride polymers; phosphorylcholine; poly n-butyl methacrylate (PBMA); polyethylene-co-vinyl acetate (PEVA); PBMA/P EVA blend or copolymer; polytetrafluoroethene (Teflon®) and derivatives; poly-paraphenylene terephthalamide (Kevlar®); poly(ether ether ketone) (PEEK); poly(styrene-b-isobutylene-b-styrene) (Translute™); tetramethyldisiloxane (side chain or copolymer); polyimides polysulfides; poly(ethylene terephthalate); poly(methyl methacrylate); poly(ethylene-co-methyl methacrylate); styrene-ethylene/butylene-styrene block copolymers; ABS; SAN; acrylic polymers and/or copolymers (e.g., n-butyl-acrylate, n-butyl methacrylate, 2-ethylhexyl acrylate, lauryl-acrylate, 2-hydroxypropyl acrylate, polyhydroxyethyl, methacrylate/methylmethacrylate copolymers); glycosaminoglycans; alkyd resins; elastin; polyether sulfones; epoxy resin; poly (oxymethylene); polyolefins; polymers of silicone; polymers of methane; polyisobutylene; ethylene-alphaolefin copolymers; polyethylene; polyacrylonitrile; fluorosilicones; poly (propylene oxide); polyvinyl aromatics (e.g. polystyrene); poly(vinyl ethers) (e.g. polyvinyl methyl ether); poly(vinyl ketones); poly(vinyl halides) (e.g. polyvinylidene fluoride, polyvinylidene chloride); poly(vinylpyrolidone); poly (vinylpyrolidone)/vinyl acetate copolymer; polyvinylpridine prolastin or silk-elastin polymers (SELP); silicone; silicone rubber; polyurethanes (polycarbonate polyurethanes, silicone urethane polymer) (e.g., chronoflex varieties, bionate varieties); vinyl halide polymers and/or copolymers (e.g. polyvinyl chloride); polyacrylic acid; ethylene acrylic acid copolymer; ethylene vinyl acetate copolymer; polyvinyl alcohol; poly(hydroxyl alkylmethacrylate); Polyvinyl esters (e.g. polyvinyl acetate); and/or copolymers, blends, and/or composites of above. Non-limiting examples of polymers that can be made to be biodegradable and/or bioresorbable with modification include, but are not limited to, hyaluronic acid (hyanluron); polycarbonates; polyorthocarbonates; copolymers of vinyl monomers; polyacetals; biodegradable polyurethanes; polyacrylamide; polyisocyanates; polyamide; and/or copolymers, blends, and/or composites of above. As can be appreciated, other and/or additional polymers and/or derivatives of one or more of the above listed polymers may be used.

In an exemplary embodiment, the nanoparticle is a single walled carbon nanotube. In another exemplary embodiment, the nanoparticle is a gold nanoparticle. In yet another exemplary embodiment, the nanoparticle is a polylactide (PLA) polymer nanoparticle. In another exemplary embodiments, the nanoparticle is the biodegradable polymer poly(lactic-co-glycolic acid) (PLGA).

Regardless of the shape, size or composition of the nanoparticle, the nanoparticle must be capable of comprising at least one nucleic acid comprising an anti-cancer nucleic acid. In some embodiments, a nanoparticle of the invention may comprise more than one anti-cancer nucleic acid. For instance, a nanoparticle may comprise at least one, two, three, four, five, six, seven, eight, or nine nucleic acids comprising an anti-cancer nucleic acid. In further embodiments, a nanoparticle may comprise a plurality of nucleic acids comprising an anti-cancer nucleic acid. For instance, in one embodiment, a nanoparticle may comprise a plurality of pSVL vectors comprising one or more UGT sequences. In a specific embodiment, a nanoparticle may comprise a plurality of pSVL vectors comprising a UGT2B15 sequence.

Nucleic acids may be attached chemically to the surface of nanoparticles by a variety of methods depending upon the composition of the nanoparticle surface. In general, the nucleic acid is attached to the nanoparticle in such a manner that it is still able to be expressed once delivered to the cell. Methods for attaching a nucleic acid to a nanoparticle for delivery into cells are known. A nucleic acid may be adsorbed to the nanoparticle surface through ionic, electrostatic, hydrophobic or other non-covalent, or chemically linked to the surface of the outer shell of the nanoparticle through covalent bonds. A nucleic acid of the invention also may be directly conjugated to the nanoparticle via a linker molecule. A linker molecule comprises at least two functional groups such that the linker molecule is disposed between the nanoparticle and the targeting moiety. By way of non-limiting example, when the nanoparticle is a carbon nanotube, the carbon nanotube may be pegylated, and the nucleic acid may be linked to the pegylated nanotube through cleavable disulfide bonds. The cleavable nature of the disulfide bond connecting the nucleic acid to the nanoparticle would deliver an expressible nucleic acid in the cell. A nucleic acid of the invention may be attached to the nanoparticle via linkage chemistry, click chemistry, and other methods known. Such attachment uses functional groups attached to the nanoparticle to link the material to the nanoparticle. By way of non-limiting example, nanoparticles may be functionalized with a first functional group or a first and a second functional group. Suitable functional groups are known in the art and include, without limitation, epoxide and amine groups. In one embodiment, a nanoparticle of the invention may comprise an epoxide group for functionalizing the nanoparticle with a nucleic acid. In another embodiment, a nanoparticle of the invention may comprise an amine group for functionalizing the nanoparticle with a nucleic acid. For example, in some embodiments, a single walled nanotube may be treated with chloroperbenzoic acid to form an epoxidized nanotube. An epoxidized nanotube may be further functionalized to form an amine functionalized-nanotube capable of strong ionic attraction to DNA. One skilled in the art will recognize the functional groups used depend upon the type and characteristics of the nanoparticle as well as those of the material to be attached.

(c) Vehicle for Delivery

In some embodiments, a composition of the invention may be further incorporated into a vehicle for cellular delivery. In these embodiments, typically a composition of the invention is encapsulated in a suitable vehicle to either aid in the delivery of the compound to target cells, to increase the stability of the composition, or to minimize potential toxicity of the composition. As will be appreciated by a skilled artisan, a variety of vehicles are suitable for delivering a composition of the present invention. Non-limiting examples of suitable structured fluid delivery systems may include liposomes, microemulsions, micelles, dendrimers and other phospholipid-containing systems. Methods of incorporating compositions into delivery vehicles are known in the art.

In one alternative embodiment, a liposome delivery vehicle may be utilized. Liposomes, depending upon the embodiment, are suitable for delivery of the composition of the invention in view of their structural and chemical properties. Generally speaking, liposomes are spherical vesicles with a phospholipid bilayer membrane. The lipid bilayer of a liposome may fuse with other bilayers (e.g., the cell membrane), thus delivering the contents of the liposome to cells. In this manner, the composition of the invention may be selectively delivered to a cell by encapsulation in a liposome that fuses with the targeted cell's membrane.

Liposomes may be comprised of a variety of different types of phosolipids having varying hydrocarbon chain lengths. Phospholipids generally comprise two fatty acids linked through glycerol phosphate to one of a variety of polar groups. Suitable phospholids include phosphatidic acid (PA), phosphatidylserine (PS), phosphatidylinositol (PI), phosphatidylglycerol (PG), diphosphatidylglycerol (DPG), phosphatidylcholine (PC), and phosphatidylethanolamine (PE). The fatty acid chains comprising the phospholipids may range from about 6 to about 26 carbon atoms in length, and the lipid chains may be saturated or unstaurated. Suitable fatty acid chains include (common name presented in parantheses) n-dodecanoate (laurate), n-tretradecanoate (myristate), n-hexadecanoate (palmitate), n-octadecanoate (stearate), n-eicosanoate (arachidate), n-docosanoate (behenate), n-tetracosanoate (lignocerate), cis-9-hexadecenoate (palmitoleate), cis-9-octadecanoate (oleate), cis,cis-9,12-octadecandienoate (linoleate), all cis-9,12,15-octadecatrienoate (linolenate), and all cis-5,8,11,14-eicosatetraenoate (arachidonate). The two fatty acid chains of a phospholipid may be identical or different. Acceptable phospholipids include dioleoyl PS, dioleoyl PC, distearoyl PS, distearoyl PC, dimyristoyl PS, dimyristoyl PC, dipalmitoyl PG, stearoyl, oleoyl PS, palmitoyl, linolenyl PS, and the like.

The phospholipids may come from any natural source, and, as such, may comprise a mixture of phospholipids. For example, egg yolk is rich in PC, PG, and PE, soy beans contains PC, PE, PI, and PA, and animal brain or spinal cord is enriched in PS. Phospholipids may come from synthetic sources too. Mixtures of phospholipids having a varied ratio of individual phospholipids may be used. Mixtures of different phospholipids may result in liposome compositions having advantageous activity or stabilty of activity properties. The above mentioned phosphoplipids may be mixed, in optimal ratios with cationic lipids, such as N-(1-(2,3-dioleolyoxy)propyl)-N,N,N-trimethyl ammonium chloride, 1,1'-dioctadecyl-3,3,3',3'-tetramethylindocarbocyanine perchloarate, 3,3'-deheptyloxacarbocyanine iodide, 1,1'-dedodecyl-3,3,3',3'-tetramethylindocarbocyanine perchloarate, 1,1'-dioleyl-3,3,3',3'-tetramethylindo carbocyanine methanesulfonate, N-4-(delinoleylaminostyryl)-N-methylpyridinium iodide, or 1,1,-dilinoleyl-3,3,3',3'-tetramethylindocarbocyanine perchloarate.

Liposomes may optionally comprise sphingolipids, in which spingosine is the structural counterpart of glycerol and one of the one fatty acids of a phosphoglyceride, or cholesterol, a major component of animal cell membranes. Liposomes may optionally, contain pegylated lipids, which are lipids covalently linked to polymers of polyethylene glycol (PEG). PEGs may range in size from about 500 to about 10,000 daltons.

Liposomes may further comprise a suitable solvent. The solvent may be an organic solvent or an inorganic solvent. Suitable solvents include, but are not limited to, dimethylsulfoxide (DMSO), methylpyrrolidone, N-methylpyrrolidone, acetronitrile, alcohols, dimethylformamide, tetrahydrofuran, or combinations thereof.

Liposomes carrying the composition of the invention (i.e., having at least one methionine compound) may be prepared by any known method of preparing liposomes for drug delivery, such as, for example, detailed in U.S. Pat. Nos. 4,241, 046, 4,394,448, 4,529,561, 4,755,388, 4,828,837, 4,925,661, 4,954,345, 4,957,735, 5,043,164, 5,064,655, 5,077,211 and 5,264,618, the disclosures of which are hereby incorporated by reference in their entirety. For example, liposomes may be prepared by sonicating lipids in an aqueous solution, solvent injection, lipid hydration, reverse evaporation, or freeze drying by repeated freezing and thawing. In a preferred embodiment the liposomes are formed by sonication. The liposomes may be multilamellar, which have many layers like an onion, or unilamellar. The liposomes may be large or small. Continued high-shear sonication tends to form smaller unilamellar lipsomes.

As would be apparent to one of ordinary skill, all of the parameters that govern liposome formation may be varied. These parameters include, but are not limited to, temperature, pH, concentration of methionine compound, concentration and composition of lipid, concentration of multivalent cations, rate of mixing, presence of and concetration of solvent.

In another embodiment, the composition of the invention may be delivered to a cell as a microemulsion. Microemulsions are generally clear, thermodynamically stable solutions comprising an aqueous solution, a surfactant, and "oil." The "oil" in this case, is the supercritical fluid phase. The surfactant rests at the oil-water interface. Any of a variety of surfactants are suitable for use in microemulsion formulations including those described herein or otherwise known in the art. The aqueous microdomains suitable for use in the invention generally will have characteristic structural dimensions from about 5 nm to about 100 nm. Aggregates of this size are poor scatterers of visible light and hence, these solutions are optically clear. As will be appreciated by a skilled artisan, microemulsions can and will have a multitude of different microscopic structures including sphere, rod, or disc shaped aggregates. In one embodiment, the structure may be micelles, which are the simplest microemulsion structures that are generally spherical or cylindrical objects. Micelles are like drops of oil in water, and reverse micelles are like drops of water in oil. In an alternative embodiment, the microemulsion structure is the lamellae. It comprises consecutive layers of water and oil separated by layers of surfactant. The "oil" of microemulsions optimally comprises phospholipids. Any of the phospholipids detailed above for liposomes are suitable for embodiments directed to microemulsions. The composition of the invention may be encapsulated in a microemulsion by any method generally known in the art.

In yet another embodiment, the composition of the invention may be delivered in a dendritic macromolecule, or a dendrimer. Generally speaking, a dendrimer is a branched tree-like molecule, in which each branch is an interlinked chain of molecules that divides into two new branches (molecules) after a certain length. This branching continues until the branches (molecules) become so densely packed that the canopy forms a globe. Generally, the properties of dendrimers are determined by the functional groups at their surface. For example, hydrophilic end groups, such as carboxyl groups, would typically make a water-soluble dendrimer. Alternatively, phospholipids may be incorporated in the surface of an dendrimer to facilitate absorption across the skin. Any of the phospholipids detailed for use in liposome embodiments are suitable for use in dendrimer embodiments. Any method generally known in the art may be utilized to make dendrimers and to encapsulate compositions of the invention therein. For example, dendrimers may be produced by an iterative sequence of reaction steps, in which each additional iteration leads to a higher order dendrimer. Consequently, they have a regular, highly branched 3D structure, with nearly uniform size and shape. Furthermore, the final size of a dendrimer is typically controlled by the number of iterative steps used during synthesis. A variety of dendrimer sizes are suitable for use in the invention. Generally, the size of dendrimers may range from about 1 nm to about 100 nm.

(d) Targeting

In some embodiments, a composition of the invention may also be targeted to a particular cell or cell type. In exemplary embodiments, a composition of the invention may be targeted to a tumor cell. Tumor cells are as described in Section (II) below. A targeted composition may comprise a targeting moiety. A targeting moiety directs or targets the composition and its attached nucleic acid cargo to a particular site or location. Targeted compositions may comprise a wide variety of targeting moieties conjugated to the outer surface of the composition, including but not limited to antibodies, antibody fragments, peptides, proteins, small molecules, polysaccharides, nucleic acids, aptamers, growth factors (such as EGF), folates, peptidomimetics, other mimetics or drugs alone or in combination. These targeting moieties may be utilized to specifically direct the composition to cellular epitopes and/or receptors. The targeting moieties may be conjugated directly or indirectly to the composition. Targeting moieties may be chemically attached to the surface of nanoparticles by a variety of methods depending upon the nature of the targeting moiety and composition of the nanoparticle surface.

II. Method of Treating a Cell

In another aspect, the invention encompasses a method of treating a cell, the method comprising contacting a cell with a composition comprising a nucleic acid comprising an anticancer nucleic acid attached to a nanoparticle. Such a composition is described in Section (I) above.

(a) Contacting a Cell

In some embodiments, a cell contacted by a composition of the invention is an in vitro cell line. In some alternative embodiments, the cell line may be a primary cell line that is not yet described. Methods of preparing a primary cell line utilize standard techniques known to individuals skilled in the art. In other alternatives, a cell line may be an established cell line. A cell line may be adherent or non-adherent, or a cell line may be grown under conditions that encourage adherent, non-adherent or organotypic growth using standard techniques known to individuals skilled in the art. A cell line may be contact inhibited or non-contact inhibited. In exemplary embodiments, a cell line is an established human cell line derived from a tumor. Non-limiting examples of cell lines derived from a tumor may include the osteosarcoma cell lines 143B, CAL-72, G-292, HOS, KHOS, MG-63, Saos-2, and U-2 OS; the prostate cancer cell lines DU145, PC3 and Lncap; the breast cancer cell lines MCF-7, MDA-MB-438 and T47D; the myeloid leukemia cell line THP-1, the glioblastoma cell line U87; the neuroblastoma cell line SHSY5Y; the bone cancer cell line Saos-2; and the pancreatic carcinoma cell line Panc1. In an exemplary embodiment, a cell contacted by a composition of the invention is derived from the pancreatic carcinoma cell line Panc1. Methods of culturing cell lines are known in the art.

In other embodiments, a cell may be contacted by a composition of the invention in vivo. Suitable subjects include, but are not limited to, mammals, amphibians, reptiles, birds, fish, and insects. In exemplary embodiments, the subject is a human.

A composition of the invention may be formulated and administered to a subject by several different means. For instance, a composition may generally be administered parenteraly, intraperitoneally, intravascularly, or intrapulmonarily in dosage unit formulations containing conventional nontoxic pharmaceutically acceptable carriers, adjuvants, and vehicles as desired. The term parenteral as used herein includes subcutaneous, intravenous, intramuscular, intrathecal, or intrasternal injection, or infusion techniques. Formulation of pharmaceutical compositions is discussed in, for example, Hoover, John E., Remington's Pharmaceutical Sciences, Mack Publishing Co., Easton, Pa. (1975), and Liberman, H. A. and Lachman, L., Eds., Pharmaceutical Dosage Forms, Marcel Decker, New York, N.Y. (1980).

Injectable preparations, for example, sterile injectable aqueous or oleaginous suspensions, may be formulated according to the known art using suitable dispersing or wetting agents and suspending agents. The sterile injectable preparation may also be a sterile injectable solution or suspension in a nontoxic parenterally acceptable diluent or solvent. Among the acceptable vehicles and solvents that may be employed are water, Ringer's solution, and isotonic sodium chloride solution. In addition, sterile, fixed oils are conventionally employed as a solvent or suspending medium. For this purpose, any bland fixed oil may be employed, including synthetic mono- or diglycerides. In addition, fatty acids such as oleic acid are useful in the preparation of injectables. Dimethyl acetamide, surfactants including ionic and non-ionic detergents, and polyethylene glycols can be used. Mixtures of solvents and wetting agents such as those discussed above are also useful.

(b) Suitable Cells

The compounds of the invention may be used to treat a neoplasm or a cancer. The neoplasm may be malignant or benign, the cancer may be primary or metastatic; the neoplasm or cancer may be early stage or late stage. Non-limiting examples of neoplasms or cancers that may be treated with a composition of the invention may include acute lymphoblastic leukemia, acute myeloid leukemia, adrenocortical carcinoma, AIDS-related cancers, AIDS-related lymphoma, anal cancer, appendix cancer, astrocytomas (childhood cerebellar or cerebral), basal cell carcinoma, bile duct cancer, bladder cancer, bone cancer, brainstem glioma, brain tumors (cerebellar astrocytoma, cerebral astrocytoma/malignant glioma, ependymoma, medulloblastoma, supratentorial primitive neuroectodermal tumors, visual pathway and hypothalamic gliomas), breast cancer, bronchial adenomas/carcinoids, Burkitt lymphoma, carcinoid tumors (childhood, gastrointestinal), carcinoma of unknown primary, central nervous system lymphoma (primary), cerebellar astrocytoma, cerebral astrocytoma/malignant glioma, cervical cancer, childhood cancers, chronic lymphocytic leukemia, chronic myelogenous leukemia, chronic myeloproliferative disorders, colon cancer, cutaneous T-cell lymphoma, desmoplastic small round cell tumor, endometrial cancer, ependymoma, esophageal cancer, Ewing's sarcoma in the Ewing family of tumors, extracranial germ cell tumor (childhood), extragonadal germ cell tumor, extrahepatic bile duct cancer, eye cancers (intraocular melanoma, retinoblastoma), gallbladder cancer, gastric (stomach) cancer, gastrointestinal carcinoid tumor, gastrointestinal stromal tumor, germ cell tumors (childhood extracranial, extragonadal, ovarian), gestational trophoblastic tumor, gliomas (adult, childhood brain stem, childhood cerebral astrocytoma, childhood visual pathway and hypothalamic), gastric carcinoid, hairy cell leukemia, head and neck cancer, hepatocellular (liver) cancer, Hodgkin lymphoma, hypopharyngeal cancer, hypothalamic and visual pathway glioma (childhood), intraocular melanoma, islet cell carcinoma, Kaposi sarcoma, kidney cancer (renal cell cancer), laryngeal cancer, leukemias (acute lymphoblastic, acute myeloid, chronic lymphocytic, chronic myelogenous, hairy cell), lip and oral cavity cancer, liver cancer (primary), lung cancers (non-small cell, small cell), lymphomas (AIDS-related, Burkitt, cutaneous T-cell, Hodgkin, non-Hodgkin, primary central nervous system), macroglobulinemia (Waldenström), malignant fibrous histiocytoma of bone/osteosarcoma, medulloblastoma (childhood), melanoma, intraocular melanoma, Merkel cell carcinoma, mesotheliomas (adult malignant, childhood), metastatic squamous neck cancer with occult primary, mouth cancer, multiple endocrine neoplasia syndrome (childhood), multiple myeloma/plasma cell neoplasm, mycosis fungoides, myelodysplastic syndromes, myelodysplastic/myeloproliferative diseases, myelogenous leukemia (chronic), myeloid leukemias (adult acute, childhood acute), multiple myeloma, myeloproliferative disorders (chronic), nasal cavity and paranasal sinus cancer, nasopharyngeal carcinoma, neuroblastoma, non-Hodgkin lymphoma, non-small cell lung cancer, oral cancer, oropharyngeal cancer, osteosarcoma/malignant fibrous histiocytoma of bone, ovarian cancer, ovarian epithelial cancer (surface epithelial-stromal tumor), ovarian germ cell tumor, ovarian low malignant potential tumor, pancreatic cancer, pancreatic cancer (islet cell), paranasal sinus and nasal cavity cancer, parathyroid cancer, penile cancer, pharyngeal cancer, pheochromocytoma, pineal astrocytoma, pineal germinoma, pineoblastoma and supratentorial primitive neuroectodermal tumors (childhood), pituitary adenoma, plasma cell neoplasia, pleuropulmonary blastoma, primary central nervous system lymphoma, prostate cancer, rectal cancer, renal cell carcinoma (kidney cancer), renal pelvis and ureter transitional cell cancer, retinoblastoma, rhabdomyosarcoma (childhood), salivary gland cancer, sarcoma (Ewing family of tumors, Kaposi, soft tissue, uterine), Sezary syndrome, skin cancers (nonmelanoma, melanoma), skin carcinoma (Merkel cell), small cell lung cancer, small intestine cancer, soft tissue sarcoma, squamous cell carcinoma, squamous neck cancer with occult primary (metastatic), stomach cancer, supratentorial primitive neuroectodermal tumor (childhood), T-Cell lymphoma (cutaneous), testicular cancer, throat cancer, thymoma (childhood), thymoma and thymic carcinoma, thyroid cancer, thyroid cancer (childhood), transitional cell cancer of the renal pelvis and ureter, trophoblastic tumor (gestational), enknown primary site (adult, childhood), ureter and renal pelvis transitional cell cancer, urethral cancer, uterine cancer (endometrial), uterine sarcoma, vaginal cancer, visual pathway and hypothalamic glioma (childhood), vulvar cancer, Waldenström macroglobulinemia, and Wilms tumor (childhood).

EXAMPLES

The following examples illustrate various iterations of the invention.

Example 1

Preparation of a Composition Comprising a Nucleic Acid Encoding a UDP-Glucuronosyltransferase Attached to a Nanoparticle Human UDP-Glucuronosyltransferases (UGTs) catalyze the glucuronidation of a variety of drugs and endogenous compounds, which serve as ligands for nuclear receptors and or signaling pathways. The most biologically significant substrates of UGTs are retinoic acid, poly unsaturated fatty acids, prostaglandins, steroids, and steroid hormones. Direct glucuronidation of those compounds control their steady state concentrations and their availability for gene regulation. In addition, environmental pollutants, endogenous steroids, and biologically active compounds synthesized in cancer cells can be substrates for UGTs. These compounds are linked to activation of nuclear receptors and signaling pathways involved in carcinogenesis and metastasis. UGTs glucuronidate these compounds, and hence are involved in the regulation of cancer cell growth. Therefore, UGTs can play an essential role in cellular detoxification and homeostasis, exert genoprotective properties and can be classified as oncogene suppressors.

UGTs are expressed in almost every tissue of the human body, including the gonads, pancreas, and spleen. However, UGT mRNA and protein levels are down regulated or completely absent in several cancer tissues, such as breast, ovarian, prostate, and pancreatic cancers. Plasmid-driven expression of UGTs in cancer cells changes the carcinogenic phenotype, arrests cancer cell growth, and results in apoptosis.

The present invention encompasses the delivery of a UGT nucleic acid using a nanoparticle. For instance, the UGT2B15 coding region was cloned into the pSVL expression vector to express UGT2B15 under the control of the SV40 promoter. The resulting plasmid was linked to carbon nanotubes (CNTs). For this study, single walled CNTs were grown by Radio-Frequency Chemical Vapor Deposition (RF-CVD) on a Fe:Ma/MgO catalyst with methane as the carbon source. The diameters of the CNTs ranged from 0.7 to 3 nm and the lengths between 100 nm to a few microns. The total purity of the nanotubes was of 99 percent or higher. The UGT2B15 expression plasmid was covalently linked to the CNTs to produce the CNT/UGT composition. The linkage of the plasmid to the CNT was in such a way that the linkage bonds do not break when introduced into biological environments.

Example 2

Contacting Target Cells with a Composition Comprising a Nucleic Acid Encoding a UDP-Glucuronosyltransferase Attached to a Carbon Nanotube Methods The composition described in Example 1 was introduced into the panc1 pancreatic cancer cell line. Several controls were carried out in parallel to determine the proper concentrations of nanoparticles with and without plasmid, and their effect on viability of panc1 cells. Panc1 human cancer cell lines were obtained from the American Type Culture Collection.

The cells were maintained in Dulbecco's modified Eagle's medium (DMEM, GIBCO) supplemented with 10% fetal calf serum, 2% L-glutamine, 1% penicillin, and 1% streptomycin stock solutions. The medium was changed every three days and the cells were treated by trypsinization before confluence. Panc1 cells were incubated with the composition for 24 hours before performing the assays described below.

To determine the percentage of dead cells after each treatment, the cells were incubated with the composition in 35 mm culture dishes at a density of $0.5 \times 10^6$ cells/dish, supplemented by DMEM medium in a humidified incubator at 37° C., and 5% $CO_2$ for 24 hours. The cells were then stained with 1× acridine orange/ethidium bromide dye and the images of the cells were captured via Light Transmission Microscopy (Olympus BX51) to determine the percentage of dead and live cells. All other chemicals were obtained form Sigma-Aldrich and used without further purification unless otherwise indicated.

Figure 1B:
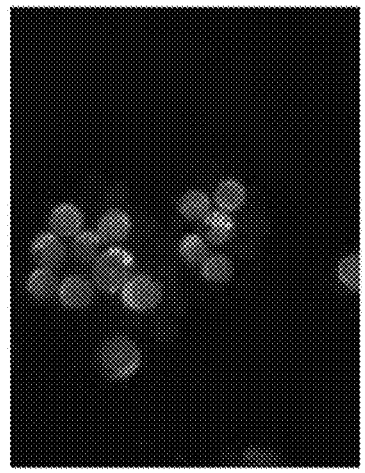
Figure 1C:
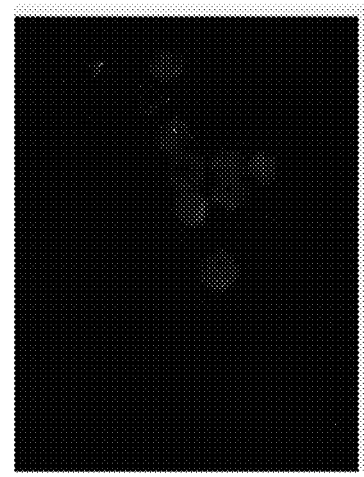

A Caspase-3 assay (FIG. 1) was also used for the assessment of apoptosis and it was performed using the Biovision GaspGLOW Red Active Caspase-3 staining kit. The cells were incubated with and without the CNTs/UGTs overnight (24 hours, then collected by scrapping and transferred to 1.5 eppendorf tubes, incubated with 1 μl of the Red-DEVD-FMK for 1 hour at 37° C. with 5% $CO_2$, and then centrifuged for 5 minutes at 3000 rpm. The supernatant was removed carefully and the cells were resuspended in 50 μl of buffer and centrifuged again. Finally, the cells were resuspended in 100 μl of the washing buffer and a few drops of the cell suspension were transferred to the microscopic slides to measure the brightness of the red stain. The brightness level of the red stain indicates the caspase-3 activation level in the cells Results Based on optical microscopy, Raman Spectroscopy, the CNTs did deliver the UGT genes inside the cells and the cells stayed active.

After incubating cells for 24 h, all (100%) of the cells that were incubated with the CNT/UGT active system died. The untreated cells (control) did not present significant changes or apoptotic behavior: only 2.7±1.2% of the control cells died, which is within the normal range. When cells were incubated with CNTs alone at concentrations identical to the ones used above, only 8.1±0.98% of the cells died, indicating only a slight toxic effect of the CNTs. It can be concluded that the CNT/UGT system was bio-active, inducing the death of the cancerous cell.

Example 3

Synthesis and Characterization of Anti-Cancer Nucleic Acid Nanodelivery System Another gene well-recognized for its role in apoptosis and cell cycle regulation is the tumor suppressor protein, p53, which in humans is encoded by the TP53 gene. P53 plays a role in apoptosis, genetic stability, and inhibition of angiogenesis. Normal cells contain two copies of functional p53 gene, and the protein produced by this gene is activated either to coordinate the DNA repair process or induce cell suicide if DNA damage proves to be irreparable. P53 can be activated in response to numerous stressors—such as DNA damage, oxidative stress, osmotic shock, ribonucleotide depletion, or deregulated oncogene expression. When the normal protective function of p53 is lost, the cells lose their potential to control growth, which results in rapid growth and a progression toward malignancy. In many types of cancers, the loss of p53 activity may also result in resistance to radiotherapy and anticancer drugs. The present invention encompasses the delivery of a p53 gene using a nanoparticle.

Methods

Carbon Nanotube Synthesis:

Single-walled carbon nanotubes were synthesized on a bi-metallic Fe—Co/MgO (2.5:2.5:95 wt. %) catalyst system. After a thorough overnight drying, the catalyst system was calcinated at 500° C. for a few hours. Next, about 50 mg of the catalyst was placed on a graphite susceptor, and the latter was inserted into a quartz tube. A radio frequency (RF) generator with a frequency of 350 kHz was utilized in the synthesis of the carbon nanotubes. Argon (Ar) was first introduced at 150 ml/min into the quartz tube positioned inside the RF coil. After 10 minutes, the RF generator was turned on. Once the temperature of the graphite susceptor reached 800° C., methane was added at 40 ml/min for 30 minutes. Next, the carbon source and the RF generator were turned off, and the sample was cooled to room temperature under the presence of Ar. The as-produced SWCNTs were mixed into a diluted HCl (1:1) solution and continuously stirred for 24 hours. Next, the SWCNT mixture was washed with DI water (until a pH of 7 was obtained) and finally dried overnight at 100° C. The purified SWCNTs were oxidized at 430° C. for 30 minutes to burn the amorphous carbon and to expose the remaining catalyst nanoparticles. Next, a second purification of SWCNTs was performed through a Nitric Acid treatment. The final product contained SWCNTs functionalized with carboxylic groups with enhanced dispersion properties in various solutions.

Characterization Techniques:

Mettler Toledo TGA/SDTA 851e was used to carry out thermogravimetric analyses (TGA) under airflow of 150 ml/min. Approximately 3 mg of the sample was heated from 25 to 850° C. at a heating rate of 5° C./min. Transmission electron microscopy (TEM) images were collected on a field emission JEM-2100F TEM (JEOL Inc.) equipped with a CCD camera and acceleration voltage of 100 kV. For TEM analysis, SWCNTs were homogeneously dispersed in 2-propanol and ultrasonicated for 30 minutes. Next, a few drops of the suspension were deposited on the TEM grid and allowed to air dry before analysis. A JEOL 7000F high-resolution scanning electron microscope was utilized to obtain scanning electron microscopy (SEM) images of the purified powdered samples. Before the microscopy analysis, the samples were mounted on aluminum pins with double-sided carbon tape.

The optical absorption spectra at UV-Vis-NIR range were recorded using the Shimadzu double beam spectrophotometer UV-3600 with three detectors. For the optical measurements, SWCNTs were individually dispersed in a sodium cholate aqueous solution. To obtain a homogeneous solution, the mixture was first sonicated for one hour (h) and then centrifuged for 2 h at 15000×g speed using a high revolution centrifuge. Only the supernatant of the final solution was utilized for optical analysis. A Horiba Jobin Yvon Model LabRam HR800 system was utilized to collect Raman Spectra of the SWCNTs. A He—Ne laser (633 nm) was used as an excitation source and the Raman shifts were calibrated with a silicon wafer at a peak of 521 $cm^{-1}$.

Synthesis of Amine Functionalized SWCNTs (f-SWCNTs):

Single-walled carbon nanotubes (SWCNTs, 50 mg) were taken in a 100 ml round-bottomed flask. To the round-bottomed flask, 50 ml dichloromethane was added. Then, m-chloroperoxybenzoic acid (1 g) was added to the round-bottomed flask. The solution was refluxed for 48 h. The solution was then filtered to collect the epoxidized SWCNTs and washed with dichloromethane (2×10 ml) and ethanol (2×10 ml). The epoxide-functionalized SWCNTs were then mixed with lithium chloride (200 mg) and 20 ml freshly distilled ethylenediamine. The mixture was then refluxed 18 h under inert atmosphere. After reflux, the reaction mixture was cooled, filtered and washed several times with ethanol (3×25 ml) in order to remove any excess ethylenediamine and lithium chloride. The resulting ethylenediamine functionalized SWCNTs were used to functionalize with p53 nucleic acids.

Functionalization of f-SWCNT with p53 Plasmid:

Protein 53 plasmids were added to a uniform DMEM (Dulbecco's Modified Eagle Medium) medium suspension of ethylenediamine functionalized single-walled carbon nanotubes (20 μg $ml^{-1}$) at 1:7.4 (p53 plasmid:f-SWCNTs) w/w ratio. The solution was then mixed thoroughly using a pipette to develop the complex of p53 and f-SWNTs.

Cell Culture:

Human breast cancer cell line MCF-7 was obtained from American Type Cell Culture. The cells were grown in a 75 $cm^2$ culture flask with DMEM (Dulbecco's Modified Eagle Medium) supplemented with 10% calf serum, 100 U $ml^{-1}$ penicillin, 100 U $ml^{-1}$ streptomycin, and 50 μg $ml^{-1}$ gentamicin sulfate and incubated with 5% $CO_2$ at 37° C. The cells were sub-cultured by trypsinization and were maintained in an aseptic condition with medium changes every 2-3 days.

Cell Treatment Protocol:

The cells were seeded at a density of $25 \times 10^4$ cells in each 35 mm cell culture dish and grown for 72 hours in normal growth medium until they reached 60-70% confluence. The medium was then removed, and cells were supplied with medium containing 20 μg $ml^{-1}$ of f-SWCNTs, 20 μg $ml^{-1}$-2.7 μg $ml^{-1}$ f-SWCNTs-p53 solution. Negative control was prepared by supplying the cell with normal growth medium. The cells were harvested for further experimental analysis after 24 h, 48 h, and 72 h of incubation. All treatments and controls were carried out in triplicate.

Cell Assessment with Light Microscopy:

The cells were plated following the protocols mentioned above for microscopy. The cells were then washed thoroughly with 10×PBS buffer solution three times and observed under light transmission microscope using a OLYMPUS BX 51 Microscope.

Results

Figure 2:
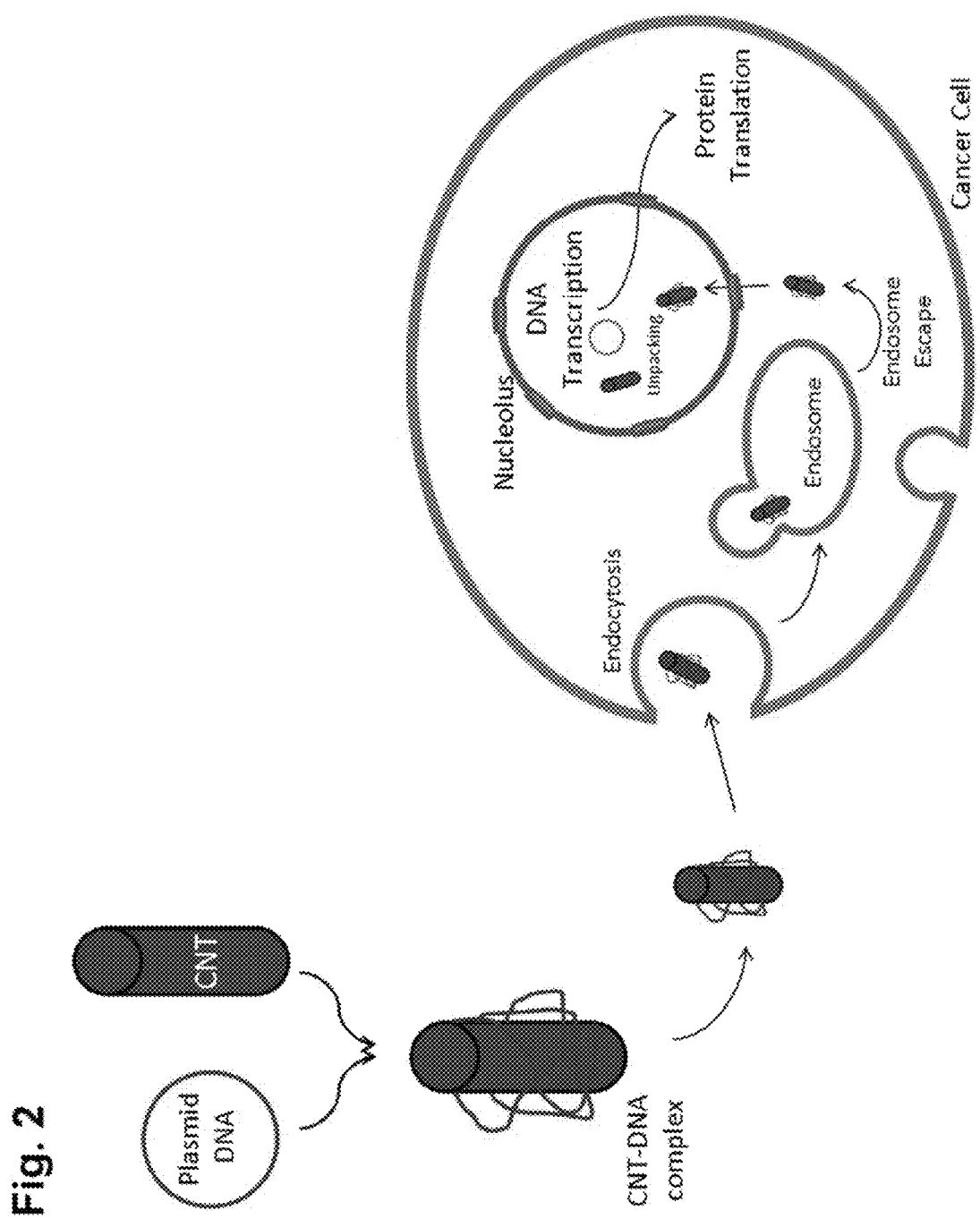
FIG. 2 illustrates f-SWCNT-p53 plasmid nanodelivery into cells.

The nanodelivery of anti-cancer nucleic acids into cancer cells occurs as depicted in FIG. 2. The internalization of f-SWCNTs-p53 complex and nucleic acid expression of p53 plasmid is a multi-step process. First, the f-SWCNTs-p53 complex enters into the cytoplasm via endocytosis and then moves to the nucleus. There, the f-SWCNTs-p53 plasmid complex dissociates as the amine groups become deprotonated due to an increase in the pH inside the nucleus. The p53 plasmid then undergoes transcription followed by transport of the transcripts to the cytoplasm where the p53 protein is transcribed. This p53 protein then activates the apoptosis pathways in the cytoplasm.

Figure 3C:
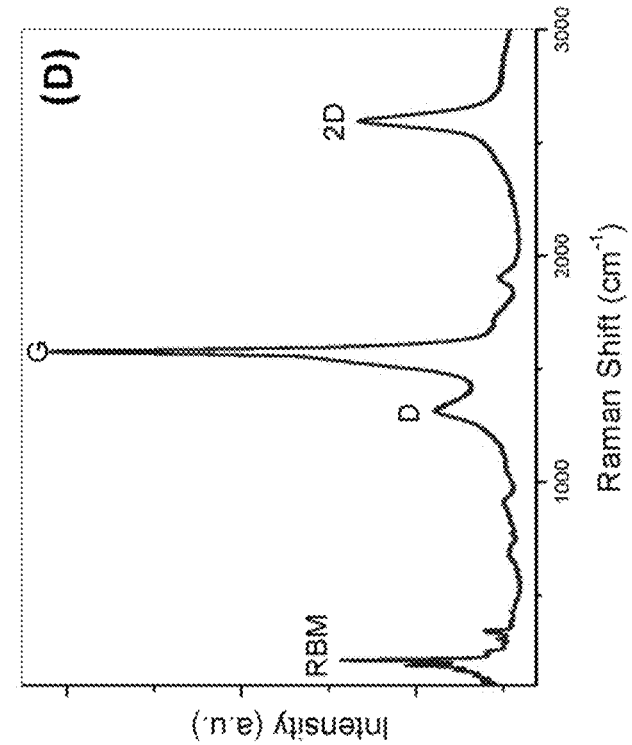
FIG. 3C and the inset show TEM images of the SWCNTs.

For Examples 2-4, fiber-like, single-walled carbon nanotubes (SWCNT) were synthesized and visualized by TEM (Transmission Electron Microscopy; Inset in FIG. 3C). Since impurities such as catalyst nano-particles or carbonaceous by-products strongly affect the electrical, mechanical and optical properties of the carbon nanotubes, high purity samples with optimal performance are necessary for various applications. Thermogravimetric analysis is a useful technique for characterizing the purity of carbon nanotubes. The weight loss profile of the SWCNTs (after purification and removal of amorphous carbon) is shown in FIG. 3A and indicated that the purity of the SWCNTs utilized was about 98.45%. Scanning electron microscope (SEM) was used to analyze the morphology of the CNT products synthesized by RF catalytic chemical vapor deposition. FIG. 3B and its inset show the SEM images of CNT bundles with an average length of several microns.

Figure 3D:
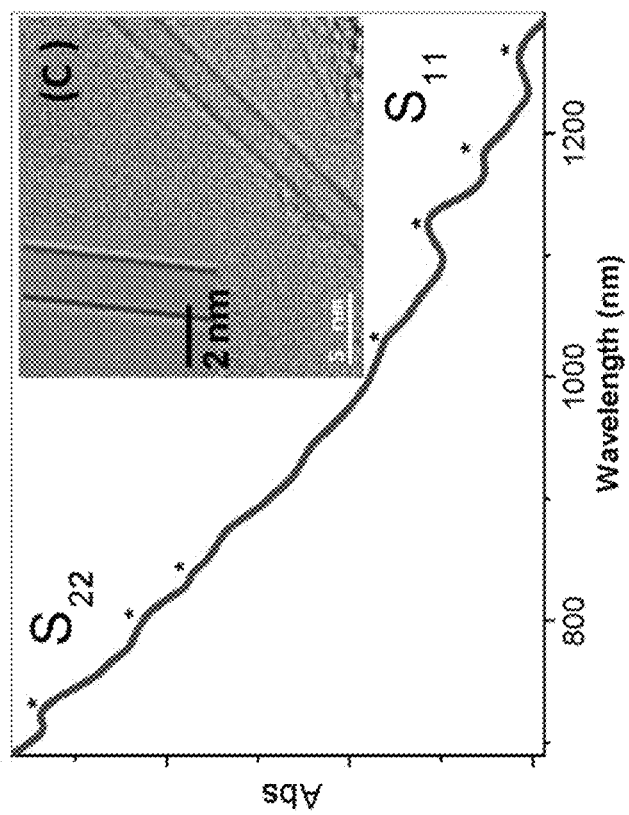
FIG. 3D shows UV-Vis-NIR spectra of SWCNTs dispersed in aqueous solution.

TEM and UV-Vis-NIR spectroscopy were utilized to analyze the diameter distribution of the SWCNTs. The inset in FIG. 3C shows the TEM images of the SWCNTs with a diameter of 2 nm. The absorption spectrum of the isolated SWCNTs is shown in FIG. 3C. The UV-Vis-NIR spectrum shows a few absorbance peaks (between 600 to 1300 nm wavelengths) in the first van Hove optical transitions ($S_{11}$) and the second van Hove transition peaks ($S_{22}$), which correspond to the absorption of the isolated SWCNTs with small diameters. TEM and optical analysis indicated that the SWCNTs utilized have diameters varying between 0.9 nm and 2.1 nm. Raman spectroscopy analyses were also performed on the purified SWCNTs to further characterize their structural properties. The peaks present in the Radial Breathing mode (RBM) are often correlated with specific diameters of single-wall carbon nanotubes. The Raman spectrum shown in FIG. 3D indicated the presence of SWCNTs with high crystallinity and with diameters between 0.7-1.7 nm. These values, which were calculated based on the RBM peaks positions present in the Raman spectra of the SWCNTs utilized, are consistent with the optical and microscopy findings.

The purified SWCNTs were treated with chloroperbenzoic acid to form epoxidized SWCNTs. This type of functional group was chosen because epoxides are highly reactive, allowing further functionalization with ethylenediamine in the presence of lithium chloride to form amine functionalized-SWCNTs (f-SWCNTs). f-SWCNTs due to presence of free amine groups on the surface remains protonated when exposed to cell culture medium. As a result, when the plasmid containing p53 DNA, which is negatively charged, is introduced to the positively charged f-SWCNTs in media. Due to the strong ionic attractions of the two components they form a well attached and stable complex. A schematic representation of the sequence of the reaction and steps involved in the production of f-SWCNT-DNA complexes is shown in FIG. 4A. Atomic force microscopy (AFM) images (FIGS. 4C and 4D) show that the f-SWCNTs are individually dispersed and successfully complexed with the p53 plasmids, visible on the sides of the nanotubes. The majority of f-SWCNTs were found to be bound with p53 plasmid when analyzed with AFM. It is also evident from the images that the plasmid DNA is not bound over the entire surface of the f-SWCNTs but is rather localized in specific areas along the length of the SWCNTs. Docking of p53 plasmids on the f-SWCNTs occurred where the highest density of protonated amine groups were present.

Example 4

Nanodelivery of Anti-Cancer Nucleic Acids into Cancer Cells

Methods

Cell Death Analysis by Ethidium Bromide and Acridine Orange Staining:

Ethidium bromide and acridine orange assays were conducted to detect the percentage of cell death. For these stainings, cells were harvested by trypsinization after appropriate incubation. They were then washed twice with 1×PBS buffer and stained with 17 µL solution of 100 mg ml$^{-1}$ acridine orange and 100 mg ml$^{-1}$ ethidium bromide in PBS and mixed together in a ratio of 1:1. A slide was prepared with all of the harvested cells and mounted with a cover slide. The stained cells were immediately visualized under UV light using an Olympus fluorescence microscope at 10× objective equipped with a digital camera. Images were taken by selecting random fields of view. The percentage of apoptosis was calculated by counting the number of live (green) and apoptotic (red) cells. Acridine orange stained the live cells, thus making them to appear green, whereas the apoptotic cells' fragmented nuclear DNA was stained by ethidium bromide and appeared red when visualized under UV light using specific light filters. Each experiment was run in triplicate, and the result has been reported as mean± standard deviation.

Green Fluorescent Protein Expression:

The cells were incubated following the protocol mentioned above using green fluorescence protein tagged p53 plasmid. Both the control and treated cells were then washed with 1×PBS buffer twice and visualized under UV light by using an Olympus fluorescence microscope at 10× objective with an FTIC filter.

Results

Using the methods and materials in Examples 2 and 3, f-SWCNT-p53 complexes were transfected into the human breast cancer cell line MCF-7. The uptake and internalization of the f-SWCNT-p53 complexes was shown by optical microscopy in FIG. 5A, which indicates that the f-SWCNTs-p53 complexes were found adhered both on the membrane and inside the cells. The agglomeration also indicated the f-SWCNTs-p53 complexes were internalized by the cell via endocytosis.

Figure 5D:
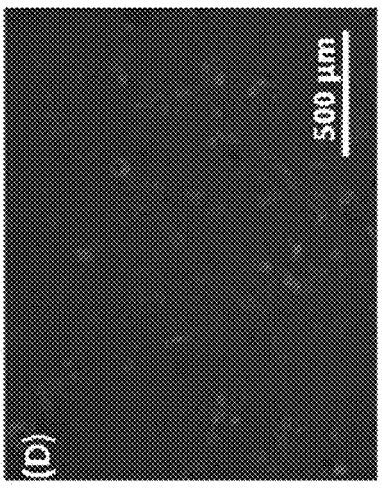
FIG. 5A depicts an optical image showing uptake of f-SWCNT-p53 complex by MCF-7 cells and agglomeration of f-SWCNT-p53 complex; B-D): Expression of GFP tagged p53 and f-SWCNT complex in MCF-7 cells after 24, 48, and 72 hours of incubation with 20 µg ml$^{-1}$ of f-SWCNTs and 2.7 µg ml$^{-1}$ of GFP tagged p53 at 37° C. and 5% $CO_2$ atmosphere.
Figure 5C:
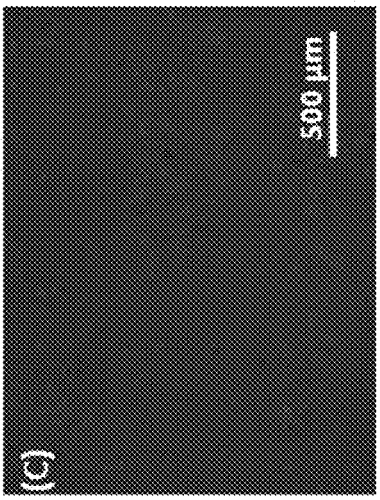
Figure 5A:
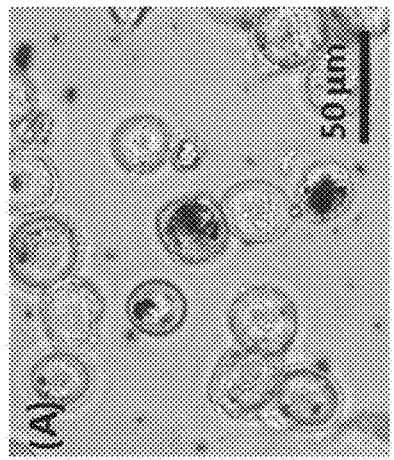
Figure 5B:
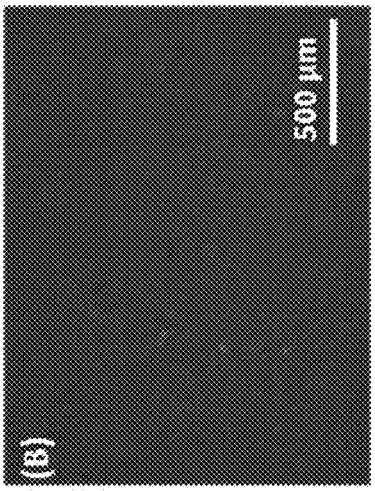

In order to follow the events occurring after treatment of the cells with the f-SWCNTs-p53 complexes, and to prove that the nucleic acids reach the nucleus of the cells, assays were conducted with f-SWCNTs complexed with plasmid coding for a p53-green fluorescence protein (GFP) fusion protein. Expression of the p53 protein was then visualized by tracking the expression of the GFP-tag (FIG. 5B-D). Protein expression, as well as the number of cells expressing GFP, was found to increase with increased incubation time with the maximum signal observed after 72 h.

Figure 6:
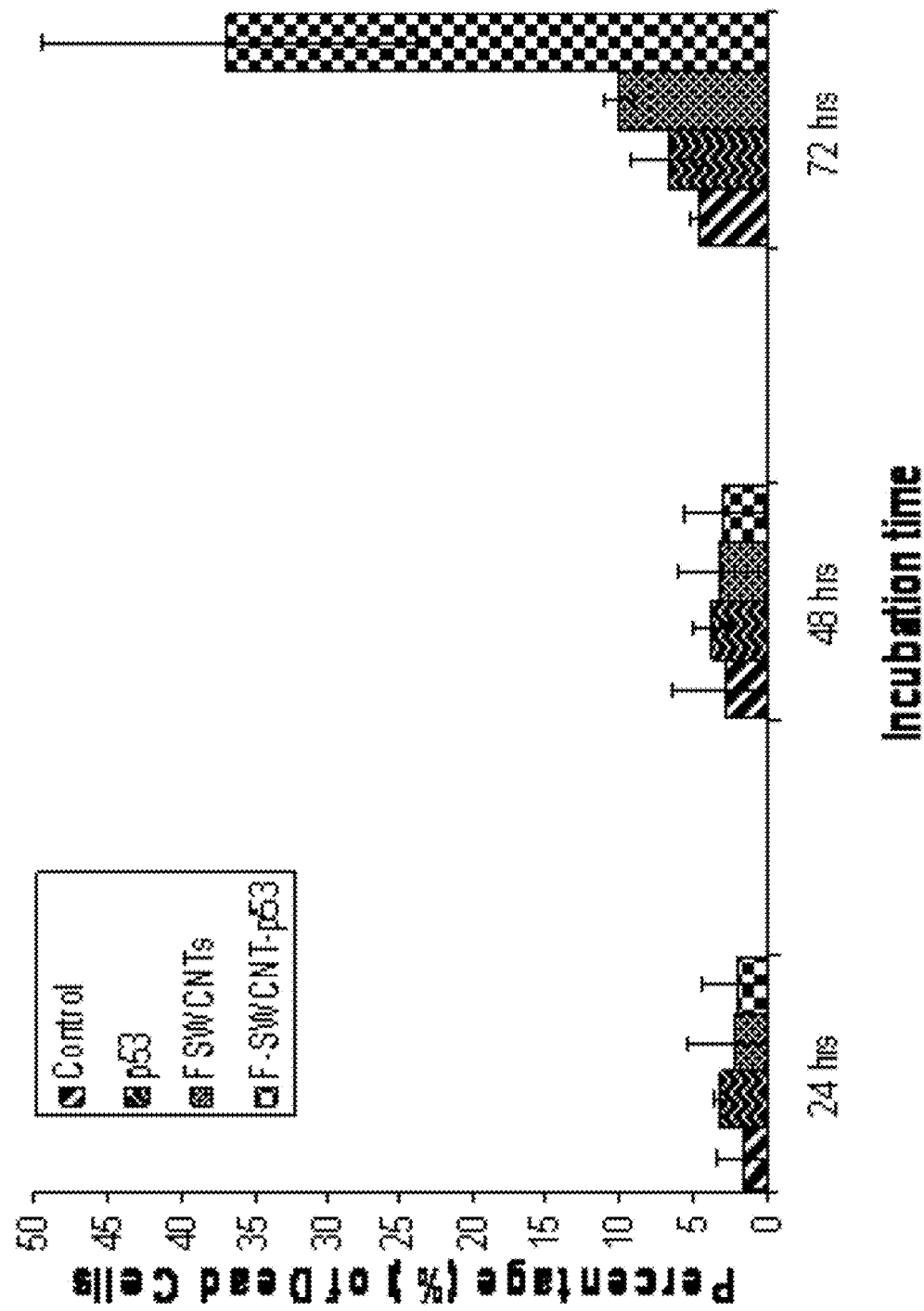
FIG. 6 graphically illustrates the percentage of dead MCF-7 cells in both control and treatment after incubation with normal growth medium and medium containing f-SWCNTs and f-SWCNTs-p53 plasmid complex.

FIGS. 6 and 7 show the result of acridine orange in conjunction with ethidium bromide to differentiate between viable and dead cells in the control and treatment group. Specifically, FIGS. 6 and 7 shows the effect of incubation time (24, 48, and 72 h) and treatment with f-SWCNTs (FIGS. 6 and 7D-F), p53 plasmid (FIGS. 7G-I) and f-SWCNT-p53 (FIGS. 7J-L) with control group (FIGS. 7A-C) on MCF-7 cells in culture. After 72 h of incubation, the apoptotic cell death percentage radically increased in cells treated with f-SWCNT-p53 and was significantly higher than that observed in the other control groups. The effect of f-SWCNT-p53 in cell death remained very similar to the control groups until 48 h of incubation, indicating that cell death was due to initiation of the apoptosis pathway by the expression of p53 and not by any toxic effect of the over-expression of the p53 protein, itself.

For the plasmid to be transcribed, it must be separated from the f-SWCNT, which is achieved by a change in the pH inside the nucleus compared to the cytoplasmic pH. This change in pH facilitates the separation of the p53 plasmids from f-SWCNTs. The positive control group where cells were incubated with 2.7 µg ml$^{-1}$ of p53 plasmid under identical experimental condition showed no induction of apoptosis. These results were very similar to the negative control group, proving that cells were going under natural apoptosis instead of induced apoptosis. f-SWCNTs were very efficient carriers for the plasmid, whereas the p53 plasmid was unable to penetrate the cells when not attached to the f-SWCNTs, as no induced apoptosis was noticed in this group. These data are also consistent the GFP expression, which showed that the 72 h incubation period provided adequate time for the plasmid to be expressed and activate the apoptotic pathways (FIG. 5B-D).

Example 5

Program Cell Death Induced in Cancer Cells by Nanodelivery of Anti-Cancer Nucleic Acids Methods
Caspase Assay:
Caspase assay was performed for the assessment of possible apoptosis by using the Biovision CaspGLOW Red Active Caspase-3 staining kit. The cells were incubated as described in previous Examples. After incubation, both the control and treated cells were trypsinized, and all of the cells were resuspended in 1 ml of normal growth medium and incubated with 1 µL of the Red-DEVD-FMK for 1 h at 37° C. with 5% $CO_2$. The cells were then centrifuged for 5 min at 3000 rpm. The cells were next resuspended and washed with wash buffer twice. Finally, the cells were resuspended in 100 µl of the washing buffer, and a microscopic slide was prepared by transferring a few drops of cell suspension. The brightness level, which indicates the level of caspase activation in the cells. was analyzed for each sample.
Results
A caspase assay was conducted to confirm the enhanced apoptosis induced by the f-SWCNT delivered wild type p53 plasmid. The negative control group showed a very negligible apoptosis signal even after 72 h (FIG. 8A-C). The cells that were treated with f-SWCNT showed results similar to those found in the negative control (FIG. 8D-F). The enhancement of the caspase signal after 72 h was not significant when compared to the f-SWCNT-p53 treated group (FIG. 8G-I), although it presented a higher signal than the negative control group.

What is claimed is:

1. An isolated pancreatic tumor cell, wherein the tumor cell comprises at least one nucleic acid attached to a nanoparticle, wherein the at least one nucleic acid is a nucleic acid encoding UGT2B15, and the nanoparticle is selected from the group consisting of a carbon nanotube, carbon nanorod, and carbon nanosphere, such that the nucleic acid is expressed within the pancreatic tumor cell.

2. The composition of claim 1, wherein the nanotube is selected from the group consisting of a single-wall carbon nanotube, a double-wall carbon nanotube, and a multi-wall carbon nanotube.

3. The composition of claim 1, wherein the nanoparticle is bio-degradable and/or bio-compatible.

4. The composition of claim 1, wherein the nucleic acid is attached to the nanoparticle using a method selected from the group consisting of covalent bonding, hydrogen bonding, click attachment, and physical attachment.

5. The composition of claim 1, wherein the nucleic acid is non-covalently attached.

6. The composition of claim 1, wherein the composition further comprises a targeting agent.

7. An ex vivo pancreatic tumor cell, wherein the tumor cell comprises at least one nucleic acid attached to a nanoparticle, wherein the at least one nucleic acid is a nucleic acid encoding UGT2B15, and the nanoparticle is selected from the group consisting of a carbon nanotube, carbon nanorod, and carbon nanosphere, such that the nucleic acid is expressed within the pancreatic tumor cell.

8. The composition of claim 7, wherein the nanotube is selected from the group consisting of a single-wall carbon nanotube, a double-wall carbon nanotube, and a multi-wall carbon nanotube.

9. The composition of claim 7, wherein the nanoparticle is bio-degradable and/or bio-compatible.

10. The composition of claim 7, wherein the nucleic acid is attached to the nanoparticle using a method selected from the group consisting of covalent bonding, hydrogen bonding, click attachment, and physical attachment.

11. The composition of claim 7, wherein the nucleic acid is non-covalently attached.

12. The composition of claim 7, wherein the composition further comprises a targeting agent.

* * * * *